US008691746B2

(12) United States Patent
Goeke et al.

(10) Patent No.: US 8,691,746 B2
(45) Date of Patent: *Apr. 8, 2014

(54) CYCLOHEXENE DERIVATIVES AND THEIR USE AS ODORANTS

(71) Applicant: Givaudan SA, Vernier (CH)

(72) Inventors: Andreas Goeke, Shanghai (CN); Yue Zou, Shanghai (CN)

(73) Assignee: Givaudan SA, Vernier (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/647,161

(22) Filed: Oct. 8, 2012

(65) Prior Publication Data
US 2013/0035278 A1 Feb. 7, 2013

Related U.S. Application Data

(63) Continuation of application No. 12/672,603, filed as application No. PCT/CH2008/000337 on Aug. 7, 2008, now Pat. No. 8,304,380.

(30) Foreign Application Priority Data

Aug. 10, 2007 (GB) .................................. 0715496.6

(51) Int. Cl.
*C07C 47/45* (2006.01)
*C07C 47/445* (2006.01)
*C07C 35/18* (2006.01)
*C07C 35/27* (2006.01)

(52) U.S. Cl.
USPC .................................. 512/1; 512/22; 512/24

(58) Field of Classification Search
USPC .................................................. 512/1, 22, 24
See application file for complete search history.

(56) References Cited

U.S. PATENT DOCUMENTS

| 3,641,156 A | 2/1972 | Pawson et al. |
| 4,010,207 A | 3/1977 | Hall |
| 8,304,380 B2 * | 11/2012 | Goeke et al. ................... 512/22 |
| 2003/0096731 A1 | 5/2003 | Lambrecht |

FOREIGN PATENT DOCUMENTS

| EP | 1214879 A | 6/2002 |
| GB | 1372021 A | 10/1974 |
| GB | 1591342 A | 6/1981 |
| JP | 63126839 A | 5/1988 |
| WO | 0143567 A | 6/2001 |
| WO | 2005087181 A2 | 9/2005 |

OTHER PUBLICATIONS

Anniina Erkkila et al., Mold Organocatalytic Methylenation of Aldehydes, Laboratory of Organic Chemistry, Helsinki University of Technology, Finland, Dec. 8, 2005.
Phila Raharivelomanana et al., Bisabolenol and B-Bisabolenol, Two New Bisabolene Sequiterpenes From Neocallitropsis Pancheri, Journal of Natural Products, Vo. 56, No. 2, pp. 272-274, Feb. 1993.
Written Opinion of the International Searching Authority for PCT/CH2008/000337 dated Jun. 19, 2009.
International Search Report for PCT/CH2008/000337 dated Jun. 19, 2009.
Barrero, "Oxygenated Sesquiterpenes from the Wood of Juniperus Oxycedrus", Phytochemistry, vol. 30, No. 5, 1991, pp. 1551-1554; Pergamon Press (Great Britain).
English language abstract for JP63126839, Apr. 30, 1988, electronically published at esp@cenet.com; European Patent Office (Europe).
English language abstract for JP63126839, Apr. 30, 1988, Thompson Scientific (London, Great Britain).
Pauluth, "Darstellung von tetramethyliertem Perillaalkohol [3,3,5,5-Tetramethyl-4-(1-methylethenyl)-1-cyclohexen-1-methanol] und verwandten Monoterpenoiden", Liebigs Ann. Chem., 1985, pp. 403-412; VCH Verlagsgesellschaft mbH, (Weinheim, Germany).
Van Der Heijden, "Structure-activity Relationships in Sweetners. I. Nitroanilines, Sulphamates, Oximes, Isocoumarins and Dipeptides", Chemical Senses, vol. 10, No. 1, pp. 57-72, 1985, IRL Press Limited (Oxford, Great Britain).
Tajima, "Development of a Neural Network Simulator for Structure-Activity Correlation of Molecules: Neco (4)—Sweet / Bitter Classification in Perillartine Derivatives", J. Chem. Software, vol. 6, No. 3, pp. 115-126, 2000, (Japan) and English language abstract.
Iwamura, " Structure-Taste Relationship of Perillartine and Nitro and Cyanoaniline Derivatives", J. Med. Chem., vol. 23, pp. 308-312, 1980, (Japan).
Suemune, "The Synthesis of 9-Substituted p-Mentha-1,8(10)-diene Derivatives", Chem. Pharm. Bull., vol. 32, pp. 4632-4636, 1984, (Japan).
Kosugi, "Synthetic Study of Marin lobane Diterpenes: Efficient Synthesis of (+)-Fuscol", J. Chem. Soc. Perkin Trans. I., pp. 217-221, 1998, (Japan).
Satsuo Kamata, "Distribution and Separation of Aniline Derivatives on a Macroreticular Sulfonated Ion exchange Resin in Nonaqueous Media", Nippon Kagakukaishi, 1973, No. 2, 292-295.
Chemical Abstracts, 1955, vol. 49, abstract No. 3082c-i, 3083a-g.
Kenji Mori, et al., "Synthesis of Compounds with Juvenile Hormone Activity", Agr. Biol. Chem., 1970, vol. 34, No. 1, 115-121.
Chemical Abstracts, 1956, vol. 50, abstract No. 885e-i.

* cited by examiner

*Primary Examiner* — Nathan M Nutter
(74) *Attorney, Agent, or Firm* — Norris McLaughlin & Marcus PA

(57) ABSTRACT

The present invention relates to a process for the production of formyl cyclohexene derivatives which are suitable as odorants as such or as intermediates for the preparation of further odorants. In particular the present invention relates to a domino-methylenation-Diels-Alder reaction of α,β-unsaturated aldehydes using formaldehyde in the presence of 1,3-butadienes.

26 Claims, No Drawings

CYCLOHEXENE DERIVATIVES AND THEIR USE AS ODORANTS

This is a Continuation patent application of U.S. Ser. No. 12/672,603 filed on 8 Feb. 2010, now U.S. Pat. No. 8,304,380, which in turn was an application filed under 35 USC 371 of PCT/CH2008/000337.

The present invention is concerned with a novel process for the production of formyl cyclohexene derivatives which are suitable for use as odorants as such or as intermediates for the preparation of further odorants. In particular, the present invention relates to a domino-methylenation-Diels-Alder reaction of α,β-unsaturated aldehydes using formaldehyde in the presence of 1,3-butadienes.

It has been known for a long time that α,β-unsaturated aldehydes can be methylenated with formaldehyde to dienes of the formula

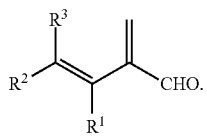

However, these dienes are unstable and rapidly dimerize. For example, R. Pummerer et al. (Liebigs Ann. 1953, 583, 161) describe the dimerization of a formylbutadiene. Similarly, the reaction of formylbutadiene with different electron-poor dienophiles was described in JP Kokoku 50-16791 of Daiichi Seiyaku Co. Due to the instability of the dienes, up to now it has only been possible to prepare formylcyclohexene derivatives crabwise. For example, the preparation of 2-acetylbuta-1,3-diene via Friedel-Crafts reaction of carbonyliron complexes and subsequent reaction with cyclopentadiene was described by F. Brion (Angew. Chem. 1981, 93, 900).

Surprisingly, inventors have now found that α,β-unsaturated aldehydes undergo an in situ methylenation using formaldehyde and that the resulting formyl butadienes undergo an organo-catalyzed Diels-Alder reaction with 1,3-butadiens, i.e. a process based on a one-pot synthesis, in which the dimerization of the formylbutadienes is suppressed.

Accordingly, the present invention refers in one of its aspects to a process comprising reacting formylbutadiene of formula B

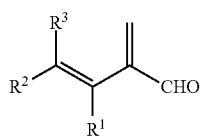

wherein $R^1$ is hydrogen, methyl, or ethyl;

$R^2$ is hydrogen, $C_1$-$C_6$ alkyl (e.g. ethyl, isopropyl), or $C_2$-$C_6$ alkenyl (e.g. 1-but-1-enyl);

$R^3$ is hydrogen, methyl, or ethyl; or either $R^1$ and $R^3$ or $R^2$ and $R^3$ form together with the carbon atoms to which they are attached a 5- or 6-membered carbocyclic ring (e.g. cyclopentenyl, cyclohexenyl);

with a diene of formula C

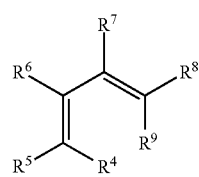

wherein $R^4$, $R^5$, $R^6$, $R^7$, $R^8$ and $R^9$ are independently selected from hydrogen, $C_1$-$C_6$ alkyl (e.g. methyl, isopropyl, tert-butyl, pentyl), or $C_2$-$C_6$ alkenyl (e.g. 2-methyl-pent-2-en-5yl, 2-methyl-prop-2-en-3-yl, 2-methyl-pent-2-en-5-yl); or $R^4$+$R^9$ together is a bivalent residue selected from —$(CH_2)_n$— wherein n is 1 or 2, —C(=C($CH_3$)$_2$)—, and —C(=C($CH_2CH_3$)$_2$)—;

resulting in compounds of formulae (Ia) and/or (Ib)

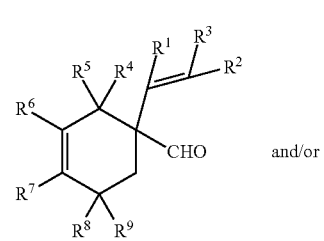

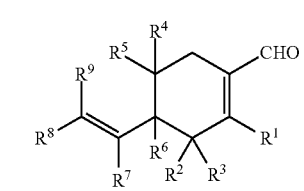

characterized in that in the presence of a methylenation catalyst and formalin the formylbutadiene of formula B is prepared in situ from an α,β-unsaturated aldehyde of formula A

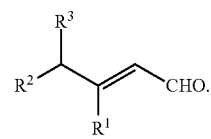

Depending on the specific properties of the diene of formula C used, either compounds of formula (Ia) or (Ib), or mixtures thereof may be prepared. For example, starting from compounds of formula C wherein $R^4$+$R^9$ together form a bivalent residue (i.e. cyclic dienes) compounds of formula (Ib) may selectively be prepared. On the other hand, compounds of formula (Ia) may selectively be prepared starting from electron-rich dienes, such as dimethyl-butadiene, whereas mixtures of compounds of formulae (Ia) and (Ib) may be prepared if electron-poor dienes, such as butadiene, isoprene or myrcene are used, as exemplified in Scheme 1 below. In the latter cases, the content of compounds (Ib) in the mixture of compounds of formulae (Ia) and (Ib) may vary from 5%-40% by weight based on the total amount of the mixture.

Scheme 1:

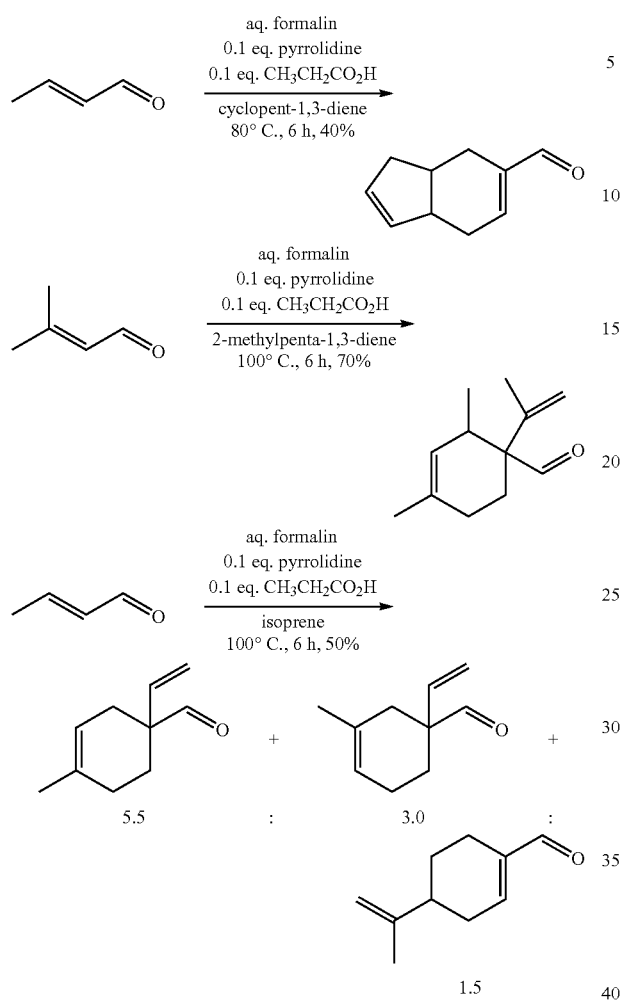

Methylenation catalysts are well known in the art. For example, a mixture of secondary amines and carboxylic acid, as described, for instance, by Anniina Erkkilä et al. in the Journal of Organic Chemistry, Vol 71, page 2538-2541, may be used. Amino acids, such as proline or derivatives thereof may also be used. The catalyst may be used in amounts from about 1 mol % to about 100 mol % based on the α,β-unsaturated aldehyde (A), preferably from about 5 mol % to about 50 mol %, e.g. 20 mol %.

In addition to the methylenation catalyst, a co-catalyst such as triphenylphosphine or other tert. phosphines, or mixtures thereof may optionally be added, which may help to increase the selectivity of the reaction and to reduce the reaction time.

Preferably the novel process is conducted at a temperature of from about 0° C. to about 120° C., e.g. at about 20° C. to about 80° C., for about 2 to 60 hours. However, by addition of a co-catalyst, the working temperature may be decreased compared to the reaction temperature of a process without a co-catalyst.

It is sometimes also practical to add an additional solvent such as toluene, DMSO, DMF or other organic solvents. For instance, in the case when 1,3-butadiene is used as diene (C), the pressure which may arise during the reaction can be reduced by adding an additional solvent. However, from an ecological point of view, a process wherein water is used as a solvent is preferred.

The reaction process of the present invention may be carried out in a reaction flask or in an autoclave.

The compounds of formulae (Ia) and (Ib) may be purified by means known to the person skilled in the art, for example, simply by separation of the organic phase followed by distillation or by extraction of the reaction mixture with organic solvents, such as MTBE (methyl tertiary-butyl ether), toluene or ethyl acetate. The remaining aqueous phase may be re-used in further reactions after it has been enriched with formaldehyde. Alternatively, the compounds of formulae (Ia) and (Ib) may be separated by chromatography, e.g. on silica gel.

The compounds of formulae (Ia) and (Ib) may be used as flavours or fragrances or they may be used as intermediates for the production of further flavour and fragrance alcohols, and derivatives thereof by reduction of the aldehydes of formulae (Ia) and (Ib) in the presence of a reducing reagent, such as $LiAlH_4$ or a Grignard reagent, resulting in compounds of formulae (IIa) and (IIb) wherein $R^{11}$ is hydrogen, optionally followed by esterification in the presence of carboxylic acid halides and a base, under conditions known to the person skilled in the art, resulting in further compounds of formulae (IIa) and (IIb)

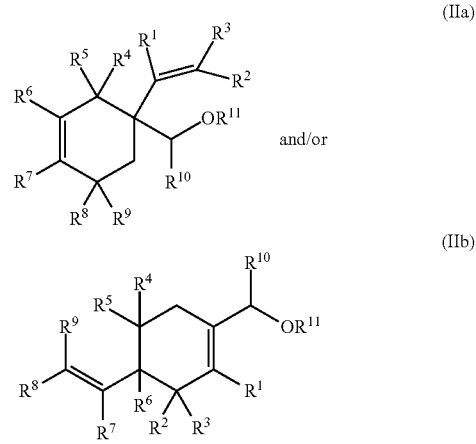

wherein
$R^1$ to $R^9$ have the same meaning as given for formulae (Ia) and (Ib);
$R^{10}$ is hydrogen, linear or branched $C_1$-$C_5$ alkyl (e.g. methyl, ethyl, isopropyl), or linear or branched $C_2$-$C_5$ alkenyl (e.g. prop-2-en-3-yl, prop-1-en-3-yl); and
$R^{11}$ is hydrogen or $COR^{12}$, wherein $R^{12}$ is hydrogen, or linear or branched $C_1$-$C_3$ alkyl (e.g. ethyl, isopropyl).

Oxidation of the compounds of formulae (IIa) and (IIb) wherein $R^{11}$=hydrogen in the presence of an oxidizing agent such as PCC (pyridinium chloro chromate) results in flavour and fragrance compounds of formulae (IIIa) and (IIIb)

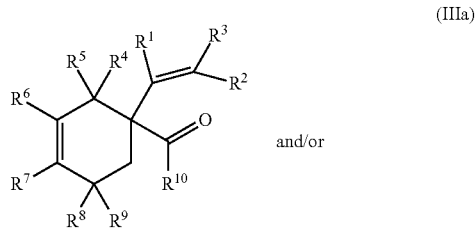

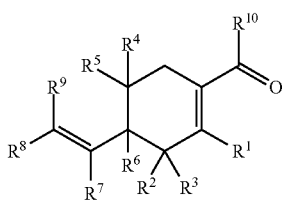
(IIIb)

wherein
R¹ to R⁹ have the same meaning as given above;
R¹⁰ is linear or branched $C_1$-$C_5$ alkyl (e.g. methyl, ethyl, isopropyl), or linear or branched $C_2$-$C_5$ alkenyl (e.g. prop-2-en-3-yl, prop-1-en-3-yl).

Transformation of the carbonyl group of the compounds of formulae (Ia), (Ib), (IIIa) and (IIIb) in the presence of a) hydroxylamine in an alcoholic solvent, such as methanol, b) methanol or ethanol, or c) diols, such as ethylene glycol or propylene glycol, results in further flavor and fragrance compounds of formulae (IVa) and (IVb) depicted herein below. The transformation of the carbonyl group takes place under conditions known to the person skilled in the art.

Using the method hereinabove described it was possible to produce known and novel compounds suitable for the use as flavors and/or fragrances. For example, it was possible to produce *perilla* aldheyde (4-(prop-1-en-2-yl)cyclohex-1-enecarbaldehyde) and *perilla* alcohol (1-(4-(prop-1-en-2-yl)cyclohex-1-enyl)ethanol) in a ecologically advantageous manner, i. e. by an organocatalytic method using water as solvent. Another example is 4-acetoxymentha-1,8-diene, which was identified by P. Schreier et al., Deutsche Lebensmittel-Rundschau 1984, 80, 335, as a volatile constituent in the enzymatic liquefaction of mango pulp. However, besides the fact that the newly-found compounds are volatile, no further properties are given. Bisabolenol ((4-(6-methylhepta-1,5-dien-2-yl)cyclohex-1-enyl)methanol) and bisabolenal (4-(6-Methylhepta-1,5-dien-2-yl)cyclohex-1-enecarbaldehyde) were found for the first time in the wood essential oil of *Neocallitropsis pancheri* by Raharivelomanana et al. (Journal of Natural Products, Vol. 56(2), 1993, 272-274). However, nothing in the literature indicates that the compounds are suitable as a flavor or fragrance ingredient. It is only known from the prior art, that sesquiterpene alcohols possess antibacterial properties, and may thus be used, for example, for the preparation of dry deodorants (WO 2005/087181).

Whereas some compounds are known as flavors or fragrances, for the majority of compounds no organoleptic properties are given in the prior art, and thus constitute a further aspect of the present invention.

Accordingly, the present invention refers in a further embodiment to the use as a flavor or a fragrance of a compound of formula (IVa)

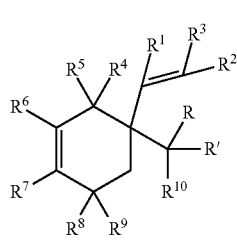
(IVa)

wherein
R¹ is hydrogen, methyl, or ethyl;
R² is hydrogen, $C_1$-$C_6$ alkyl (e.g. ethyl, isopropyl), or $C_2$-$C_6$ alkenyl (e.g. 1-but-1enyl);
R³ is hydrogen or methyl; or
either R¹ and R³ or R² and R³ form together with the carbon atoms to which they are attached a 5- or 6-membered carbocyclic ring (e.g. cyclopentenyl or cyclohexenyl);
R⁴, R⁵, R⁶, R⁷, R⁸ and R⁹ are independently selected from hydrogen, linear or branched $C_1$-$C_6$ alkyl (e.g. methyl, isopropyl, tert-butyl, pentyl), or linear or branched $C_2$-$C_6$ alkenyl (e.g. 2-methyl-pent-2-en-5-yl, 2-methyl-prop-2-en-3-yl);
R¹⁰ is hydrogen, $C_1$-$C_5$ alkyl (e.g. methyl, isopropyl, pentyl), or $C_2$-$C_5$ alkenyl (e.g. prop-1-en-3-yl, prop-2-en-3-yl, 2-methyl-prop-1-en-3-yl); and
R is hydrogen and R' is selected from hydroxyl or —OCOR¹³, wherein R¹³ is hydrogen, or $C_1$-$C_3$ alkyl (e.g. ethyl, isopropyl),
R and R' are selected from methoxy and ethoxy, or
R and R' forming together with the carbon atom to which they are attached dioxolan, dioxane, carbonyl, or C=N—OH;
with the proviso that 4-acetoxymentha-1,8-diene and compound(s) of formula (IVa) wherein R¹, R⁴ to R⁶, R⁸ and R⁹ are hydrogen, R⁷ is methyl and R+R' forms together with the carbon atom to which they are attached carbonyl or R is hydrogen and R' is hydroxyl are excluded.

Non-limiting examples are those compounds of formula (IVa) wherein at least two of R⁴, R⁵, R⁶, R⁷, R⁸, and R⁹ are not hydrogen, for example, compounds of formula (IVa) wherein R⁴ and R⁷ are methyl and R⁵, R⁶, R⁸, and R⁹ are hydrogen.

Further non-limiting examples are those compounds of formula (IVa) wherein two of R⁴, R⁵, R⁶, R⁷, R⁸, and R⁹ are methyl, preferably R⁴ and R⁷ are methyl, and R¹ is hydrogen or methyl.

Further non-limiting examples are those compounds of formula (IVa) wherein R¹ is hydrogen and R² is $C_1$-$C_6$ alkyl (e.g. ethyl, isopropyl), or $C_2$-$C_6$ alkenyl (e.g. 1-but-1enyl), preferably methyl, and R³ is hydrogen or methyl.

The compounds of formula (IVa) possess floral, fruity odor notes.

In particular embodiments compounds of formula (IVa) may be selected from
2,4-dimethyl-1-vinylcyclohex-3-enecarbaldehyde,
(2,4-dimethyl-1-vinylcyclohex-3-enyl)methanol,
(2,4-dimethyl-1-vinylcyclohex-3-enyl)ethanol,
1-(2,4-dimethyl-1-vinylcyclohex-3-enyl)ethanone,
(2,4-dimethyl-1-vinylcyclohex-3-enyl)methyl acetate,
(2,4-dimethyl-1-vinylcyclohex-3-enyl)but-3-en-1-ol,
(2,4-dimethyl-1-vinylcyclohex-3-enyl)but-3-en-1-one,
2,4-dimethyl-1-(prop-1-en-2-yl)cyclohex-3-enecarbaldehyde,
1-(2,4-dimethyl-1-(prop-1-en-2-yl)cyclohex-3-enyethanol,
1-(2,4-dimethyl-1-(prop-1-en-2-yl)cyclohex-3-enyethyl acetate,
1-(2,4-dimethyl-1-(prop-1-en-2-yl)cyclohex-3-enyl)-2-methylpropan-1-ol,
1-(2,4-dimethyl-1-(prop-1-en-2-yl)cyclohex-3-enyl)-2-methylpropan-1-one,
1-(2,4-dimethyl-1-(prop-1-en-2-yl)cyclohex-3-enyl)ethanone,
1-(2,4-dimethyl-1-(prop-1-en-2-yl)cyclohex-3-enyl)but-3-en-1-ol,
1-(2,4-dimethyl-1-(prop-1-en-2-yl)cyclohex-3-enyl)but-3-en-1-one, 1-(2,4-dimethyl-1-(prop-1-en-2-yl)cyclohex-3-enyl)but-2-en-1-one,
1-(buta-1,3-dienyl)-2,4-dimethylcyclohex-3-enecarbaldehyde,
3,4-dimethyl-1-vinylcyclohex-3-enecarbaldehyde,
2-methyl-1-(2-methylprop-1-enyl)cyclohex-3-enecarbaldehyde,
2,4-dimethyl-1-(2-methylprop-1-enyl)cyclohex-3-enecarbaldehyde,
1-(2,4-dimethyl-1-(2-methylprop-1-enyl)cyclohex-3-enyl)ethanol,
1-cyclopentenyl-2,4-dimentylcyclohex-3-enecarbaldehyde,
4,5-dimethyl-2-(2-methylprop-1-enyl)-1-vinylcyclohex-3-enecarbaldehyde,
2-methyl-4-(4-methylpent-3-enyl)-1-vinylcyclohex-3-enecarbaldehyde,
3-methyl-1-vinyl-cyclohex-3-ene-carbaldehyde,
4-methyl-1-vinyl-cyclohex-3-enecarbaldehyde oxime,
3-methyl-1-vinyl-cyclohex-3-ene-carbaldehyde oxime,
1-(prop-1-en-2-yl)cyclohex-3-enecarbaldehyde,
1-(but-1-enyl)-2,4-dimethylcyclohex-3-enecarbaldehyde,
4-methyl-1-(prop-1-en-2-yl)cyclohex-3-enecarbaldehyde,
3-methyl-1-(prop-1-en-2-yl)cyclohex-3-enecarbaldehyde, and
1-vinylcyclohex-3-ene carbaldehyde, or mixtures thereof.

In a further aspect the present invention refers to the use as flavor or fragrance of a compound of formula (IVb)

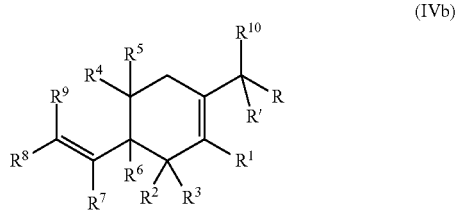

(IVb)

wherein
R$^1$ is hydrogen, methyl, or ethyl;
R$^2$ is hydrogen, C$_1$-C$_6$ alkyl (e.g. ethyl, isopropyl), or C$_2$-C$_6$ alkenyl (e.g. 1-but-1enyl);
R$^3$ is hydrogen or methyl; or
either R$^1$ and R$^3$ or R$^2$ and R$^3$ form together with the carbon atoms to which they are attached a 5- or 6-membered carbocyclic ring (e.g. cyclopentyl);
R$^4$, R$^5$ and R$^6$ are hydrogen;
R$^7$ and R$^8$ are independently hydrogen, C$_1$-C$_6$ alkyl (e.g. methyl, tert-butyl, pentyl), or C$_2$-C$_6$ alkenyl (e.g. 2-methylpent-2-en-5yl);
R$^9$ is hydrogen, methyl or ethyl; or
R$^4$+R$^9$ together is a bivalent residue selected from —(CH$_2$)$_n$— wherein n is 1 or 2, —C(=C(CH$_3$)$_2$)—, and C(=C(CH$_2$CH$_3$)$_2$)—;
R$^{10}$ is hydrogen, C$_1$-C$_5$ alkyl (e.g. methyl, ethyl, isopropyl, pentyl), or C$_2$-C$_5$ alkenyl (e.g. prop-1-en-3-yl, prop-2-en-3-yl, 2-methyl-prop-1-en-3-yl); and
R is hydrogen and R' is selected from hydroxyl or —OCOR$^{13}$, wherein R$^{13}$ is hydrogen, or C$_1$-C$_3$ alkyl (e.g. ethyl, isopropyl),
R and R' are selected from methoxy and ethoxy, or
R and R' forming together with the carbon atom to which they are attached dioxolan, dioxane, carbonyl, or C=N—OH;

provided that compounds of formula (IVb) wherein R$^1$-R$^6$, R$^8$ and R$^9$ are hydrogen and R$^7$ is methyl are excluded.

Non-limiting examples are those compounds of formula (IVb) wherein R$^3$, R$^4$, R$^5$ and R$^9$ are hydrogen, and R and R' form together with the carbon atom to which they are attached carbonyl or R is hydrogen and R' is hydroxyl.

Further non-limiting examples are those compounds of formula (IVb) wherein R$^3$ and R$^5$ are hydrogen, R$^6$ and R$^7$ are independently selected from hydrogen and methyl, and R$^4$+R$^9$ together is a bivalent residue selected from —(CH$_2$)$_n$— wherein n is 1 or 2, —C(=C(CH$_3$)$_2$)—.

Further non-limiting examples are those compounds of formula (IVb) wherein R$^{10}$ is hydrogen or methyl and R and R' form together with the carbon atom to which they are attached carbonyl or C=N—OH.

Further non-limiting examples are those compounds of formula (IVb) wherein R$^{10}$ and R are independently selected from hydrogen or methyl, and R' is hydroxyl.

The compounds of formula (IVb) possess green odor notes.

In particular embodiments compounds of formula (IVa) may be selected from
4-vinylcyclohex-1-ene carbaldehyde,
(4-vinylcyclohex-1-enyl)methanol,
1-(4-vinylcyclohex-1-enyl)ethanol,
2-methyl-4-vinylcyclohex-1-ene carbaldehyde,
(2-methyl-4-vinylcyclohex-1-enyl)methanol,
3a,4,7,7a-tetrahydro-1H-indene-6-carbaldehyde,
3a,4,7,7a-tetrahydro-1H-indene-6-carbaldehyde oxime,
(3a,4,7,7a-tetrahydro-1H-inden-6-yl)methanol,
1-(3a,4,7,7a-tetrahydro-1H-inden-6yl)ethanone,
5-methyl-3a,4,7,7a-tetrahydro-1H-indene-6-carbaldehyde,
(5-methyl-3a,4,7,7a-tetrahydro-1H-inden-6-yl)methanol,
1-(propan-2-ylidene)-3a,4,7,7a-tetrahydro-1H-indene-6-carbaldehyde,
2-methyl-3a,4,7,7a-tetrahydro-1H-indene-6-carbaldehyde,
3-methyl-3a,4,7,7a-tetrahydro-1H-indene-6-carbaldehyde,
4-ethyl-3a,4,7,7a-tetrahydro-1H-indene-6-carbaldehyde,
1,4,4a,7,8,8a-hexahydronaphthalene-2-carbaldehyde, and
4-(6-methylhepta-1,5-dien-2-yl)cyclohex-1-enecarbaldehyde, or mixtures thereof.

Whereas some compounds falling under the general formula (IVa) or (IVb) have been described in the literature, most of them have not, and are therefore novel. For example, the preparation of 1-(3a,4,7,7a-tetrahydro-1H-inden-6yl)ethanone, i.e. a compound of formula (IVb) wherein R$^1$ to R$^8$, and R$^{10}$ are hydrogen, R and R' forming together with the carbon atom to which they are attached carbonyl, and R$^4$+R$^9$ together is methylene, is described by F. Brion et al. (Angew. Chem, 1981, 93, 900). However, the prior art remains silent with regard to any organoleptic properties.

Thus, in another aspect of the invention, there is provided a compound of formula (IVa)

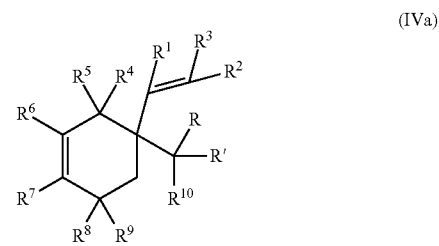

(IVa)

wherein
R¹ is hydrogen, methyl, or ethyl;
R² is hydrogen, $C_1$-$C_6$ alkyl (e.g. ethyl, isopropyl), or $C_2$-$C_6$ alkenyl (e.g. 1-but-1enyl);
R³ is hydrogen or methyl; or
either R¹ and R³ or R² and R³ form together with the carbon atoms to which they are
attached a 5- or 6-membered carbocyclic ring (e.g. cyclopentenyl or cyclohexenyl);
R⁴, R⁵, R⁶, R⁷, R⁸ and R⁹ are independently selected from hydrogen, linear or branched $C_1$-$C_6$ alkyl (e.g. methyl, isopropyl, tert-butyl, pentyl), or linear or branched $C_2$-$C_6$ alkenyl (e.g. 2-methyl-pent-2-en-5-yl, 2-methyl-prop-2-en-3-yl);
R¹⁰ is hydrogen, $C_1$-$C_5$ alkyl (e.g. methyl, isopropyl, pentyl), or $C_2$-$C_5$ alkenyl (e.g. prop-1-en-3-yl, prop-2-en-3-yl, 2-methyl-prop-1-en-3-yl); and
R is hydrogen and R' is selected from hydroxyl or —OCOR¹³, wherein R¹³ is hydrogen, or $C_1$-$C_3$ alkyl (e.g. ethyl, isopropyl),
R and R' are selected from methoxy and ethoxy, or
R and R' forming together with the carbon atom to which they are attached dioxolan, dioxane, carbonyl, or C=N—OH;
with the proviso that 4-acetoxymentha-1,8-diene and compound(s) of formula (IVa) wherein R¹, R⁴ to R⁶, R⁸ and R⁹ are hydrogen, R⁷ is methyl and R+R' form together with the carbon atom to which they are attached carbonyl or R is hydrogen and R' is hydroxyl are excluded.

The present invention refers in a further aspect to compounds of formula (IVb)

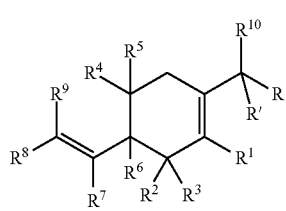

(IVb)

wherein
R¹ is hydrogen, methyl, or ethyl;
R² is hydrogen, $C_1$-$C_6$ alkyl (e.g. ethyl, isopropyl), or $C_2$-$C_6$ alkenyl (e.g. 1-but-1 enyl);
R³ is hydrogen or methyl; or
either R¹ and R³ or R² and R³ form together with the carbon atoms to which they are attached a 5- or 6-membered carbocyclic ring (e.g. cyclopentyl);
R⁴, R⁵ and R⁶ are hydrogen;
R⁷ and R⁸ are independently hydrogen, $C_1$-$C_6$ alkyl (e.g. methyl, tert-butyl, pentyl), or $C_2$-$C_6$ alkenyl (e.g. 2-methyl-pent-2-en5yl);
R⁹ is hydrogen, methyl or ethyl; or
R⁴+R⁹ together is a bivalent residue selected from —(CH₂)ₙ— wherein n is 1 or 2, —C(=C(CH₃)₂)—, and —C(=C(CH₂CH₃)₂)—;
R¹⁰ is hydrogen, $C_1$-$C_5$ alkyl (e.g. methyl, ethyl, isopropyl, pentyl), or $C_2$-$C_5$ alkenyl (e.g. prop-1-en-3-yl, prop-2-en-3-yl, 2-methyl-prop-1-en-3-yl); and
R is hydrogen and R' is selected from hydroxyl or —OCOR¹³, wherein R¹³ is hydrogen, or $C_1$-$C_3$ alkyl (e.g. ethyl, isopropyl), R and R' are selected from methoxy and ethoxy, or
R and R' forming together with the carbon atom to which they are attached dioxolan, dioxane, carbonyl, or C=N—OH;
provided that 1-(3a,4,7,7a-tetrahydro-1H-inden-6yl)ethanone, compounds of formula (IVb) wherein R¹-R⁶, R⁸ and R⁹ are hydrogen and R⁷ is methyl or 2-methyl-pent-2-en-5-yl are excluded.

As used in relation to compounds of formulae (IIa) to (IVa) and (Ib) to (IVb) unless otherwise indicated "alkyl" and "alkenyl" refers to linear and branched alkyls and alkenyls.

The compounds of formulae (IVa) and (IVb) may be used alone or in combination with a base material. As used herein, the "base material" includes all known odorant molecules selected from the extensive range of natural and synthetic molecules currently available, such as essential oils and extracts, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, and other auxiliary agents commonly used in the art, e.g., solvents such as dipropylene glycol, isopropyl myristate, and triethyl citrate.

As used herein, "fragrance composition" means any composition comprising at least one compound selected from compounds of formulae (IVa) and (IVb) and a base material, e.g. a diluent conventionally used in conjunction with odorants, such as dipropyleneglycol (DPG), isopropylmyristate (IMP), triethylcitrate (REC), diethylphthalate (DEP) and alcohol (e.g. ethanol).

The following list comprises examples of known odorant molecules, which may be combined with the compounds of the present invention:
  essential oils and extracts, e.g. oak moss absolute, basil oil, tropical fruit oils, such as bergamot oil and mandarine oil, mastic absolute, myrtle oil, palmarosa oil, patchouli oil, petitgrain oil, wormwood oil, lavender oil, rose oil, jasmin oil, ylang-ylang oil and sandalwood oil.
  alcohols, e.g. cis-3-hexenol, cinnamic alcohol, citronellol, Ebanol®, eugenol, farnesol, geraniol, menthol, nerol, rhodinol, Super Muguet™, linalool, phenylethyl alcohol, Sandalore®, terpineol and Timberol®(1-(2,2,6-Trimethylcyclohexyphexan-3-ol).
  aldehydes and ketones, e.g. citral, hydroxycitronellal, Lilial®, methylnonylacetaldehyde, anisaldehyde, allylionone, verbenone, nootkatone, geranylacetone, α-amyl cinnamic aldehyde, Georgywood™, hydroxycitronellal, Iso E Super®, Isoraldeine®(methylionone), Hedione®, maltol, methyl cedryl ketone, and vanillin.
  ethers and acetals, e.g. Ambrox®, geranyl methyl ether, rose oxide or Spirambrene®.
  esters and lactones, e.g. benzyl acetate, cedryl actetate, γ-decalactone, Helvetolide®, γ-undecalactone, vetivenyl acetate, cinnamyl propionate, citronellyl acetate, decyl acetate, dimethylbenzylcarbinyl acetate, ethyl acetoacetate, cis-3-hexenyl isobutyrate, linalyl acetate and geranyl acetate.
  macrocycles, e.g. ambrettolide, ethylene brassylate or Exaltolide®.
  heterocycles, e.g. isobutylquinoline.

The compounds of formulae (IVa) and (IVb), or mixtures thereof may be used in a broad range of fragrance applications, e.g. in any field of fine and functional perfumery, such as perfumes, household products, laundry products, body care products and cosmetics. The compounds can be employed in widely varying amounts, depending upon the specific application and on the nature and quantity of other odorant ingredients. The proportion is typically from 0.0001 to 2 weight percent of the application. In one embodiment, compounds of the present invention may be employed in a fabric softener in an amount of from 0.0001 to 0.005 weight percent. In another embodiment, the compounds may be used in an alcoholic solution in amounts of from 0.01 to 3 weight percent, more preferably between 0.5 and 2 weight percent. However, these values are given only by way of example, since the experienced perfumer may also achieve effects or may create novel accords with lower or higher concentrations, e.g. up to about 20 weight percent based on the fragrance composition.

The compounds of formulae (IVa) and (IVb), or mixtures thereof may be employed in a consumer product base by directly mixing the compound, a mixture thereof, or a fragrance composition with the consumer product base, or they may, in an earlier step, be entrapped with an entrapment material such as polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the application.

Thus, the invention additionally provides a method of manufacturing a fragrance application, comprising the incorporation of a compound of formula (IVa) and/or formula (IVb), as a fragrance ingredient, either by directly admixing the compound to the consumer product base of by admixing a fragrance composition comprising a compound of formula (IVa) and/or a compound of formula (IVb), or precursors thereof, which may then be admixed with a consumer product base, using conventional techniques and methods.

Through the addition of an olfactory acceptable amount of a compound of formula (IVa) and/or a compound of formula (IVb), the odour notes of a consumer product base will be improved, enhanced or modified.

By "precursors" is meant, in particular, reaction products of a compound of formula (IVa) or (IVb) with a compound comprising at least one functional group selected from the group of primary amine, secondary amine, sulfhydryl (thiol), hydroxyl and carboxyl, in which a covalent bond is formed between at least one carbon atom of the compound of formulae (IVa) and (IVb) respectively and at least one of the hetero atoms (N, S and O) of said compounds comprising at least one functional.

In a further aspect, the invention provides a method for improving, enhancing or modifying a consumer product base by means of the addition thereto of an olfactory acceptable amount of a compound selected from compounds of formulae (IVa) and (IVb), or mixtures thereof.

The invention also provides a fragrance application comprising:
 a) as odorant a compound selected from compounds of formulae (IVa) and (IVb), and mixtures thereof; and
 b) a consumer product base.

As used herein, "consumer product base" means a composition for use as a consumer product to fulfill specific actions, such as cleaning, softening, and caring or the like. Examples of such products include fine perfumery, e.g. perfume and eau de toilette; fabric care, household products and personal care products such as laundry care detergents, rinse conditioner, personal cleansing composition, detergent for dishwasher, surface cleaner; laundry products, e.g. softener, bleach, detergent; body care products, e.g. shampoo, shower gel; air care products and cosmetics, e.g. deodorant, vanishing creme.

This list of products is given by way of illustration and is not to be regarded as being in any way limiting.

The invention is now further described with reference to the following non-limiting examples. These examples are for the purpose of illustration only and it is understood that variations and modifications can be made by one skilled in the art.

EXAMPLE 1

2,4-Dimethyl-1-vinylcyclohex-3-enecarbaldehyde

To a mixture of crotonic aldehyde (165.2 g, 2.36 mol), 2-methyl-penta-1,3-diene (361.6 g, 4.41 mol) and formalin (37% in water (200 g, 2.46 mol) was added a mixture of pyrrolidine (16.0 g, 0.22 mol) and propionic acid (17.0 g, 0.23 mol). The mixture was placed in an autoclave and heated to 60-100° C. for 8 h. The reaction mixture was cooled to room temperature, diluted with sat. $NaHCO_3$ and extracted 3 times with MTBE (200 ml). The combined org. layers were washed with brine (200 ml), dried ($MgSO_4$) and evaporated in vacuo. The residue was purified by distillation to give 2,4-dimethyl-1-vinylcyclohex-3-enecarbaldehyde (50% yield). Boiling point: 50-53° C./0.15 mbar.

Odor description: green, fresh, camphoraceous.

$^1$H-NMR (300 MHz, $CDCl_3$): 9.52 (s, 1H, CHO), 5.79 (dd, J=10.9, 17.7 Hz, 1H, CH=$CH_2$), 5.36 (bs, 1H, 3-H), 5.30 (d, J=10.9 Hz, 1H, CH=$CH_cH_t$), 5.11 (d, J=17.7 Hz, 1H, CH=$CH_cH_t$), 2.49 (bs, 1H, 2-H), 2.01-1.90 (m, 2H), 1.74-1.59 (m, 2H), 1.66 (bs, 3H, 4-$CH_3$), 1.02 (d, J=7.1 Hz, 3H, 2-$CH_3$) ppm. $^{13}$C-NMR (75 MHz, $CDCl_3$): 202.9 (d, CHO), 138.4 (d, CH=$CH_2$), 134.0 (s, C-4), 124.7 (d, C-3), 177.6 (t, CH=$CH_2$), 54.2 (s, C-1), 34.8 (d, C-2), 27.1 (t, C-5), 24.9 (t, C-6), 23.3 (q, 4-$CH_3$), 17.1 (q, 2-$CH_3$) ppm. GC/MS (EI), endo-isomer (major): 164 (M+, 11), 149 (10), 135 (22), 107 (51), 93 (38), 82 (100), 67 (86), 55 (24), 41 (26). IR (neat, v/cm$^{-1}$): 2965 s, 2933 s, 2729 w, 1722 s, 1631 w, 1451 m, 921 m.

EXAMPLE 2

(2,4-Dimethyl-1-vinylcyclohex-3-enyl)methanol

To a suspension of $LiAlH_4$ (0.114 g, 30 mmol) in diethylether (20 ml) was added a solution of 2,4-dimethyl-1-vinylcyclohex-3-enecarbaldehyde (56 mmol) in diethylether (10 ml) at 5° C. The mixture was stirred at room temperature for 1 h. 0.1 ml of water, 0.1 ml 16% aq. NaOH and 0.3 ml of water were carefully added dropwise. The mixture was stirred for 2 h, was then filtered and concentrated in vacuo. The residue was purified by chromatography to give (2,4-dimethyl-1-vinylcyclohex-3-enyl)methanol (76% yield).

Odor description: floral, iris-like, woody.

$^1$H-NMR (300 MHz, $CDCl_3$): 5.75 (dd, J=10.9, 17.7 Hz, 1H, CH=$CH_2$), 5.23 (bs, 1H, 3-H), 5.19 (d, J=10.9 Hz, 1H, CH=$CH_cH_t$), 5.13 (d, J=17.7 Hz, 1H, CH=$CH_cH_t$), 3.50 (d, J=10.9 Hz, 1H, $CH_aH_bO$), 3.42 (d, J=10.9 Hz, 1H, $CH_aH_bO$), 2.21 (bs, 1H, 2-H), 2.02-1.86 (m, 3H), 1.74-1.55 (m, 1H), 1.62 (s, 3H), 1.42-1.32 (m, 1H), 0.91 (d, J=7.2 Hz, 3H, 2-$CH_3$) ppm. GC/MS (EI): 166 (M$^+$, 2), 148 (11), 135 (28), 120 (11), 107 (27), 91 (27), 82 (100), 67 (59), 55 (14), 41 (15).

EXAMPLE 3

(2,4-Dimethyl-1-vinylcyclohex-3-enyl)ethanol

To a solution of methylmagnesium bromide (40 mmol, 1 M in THF) was added a solution of 2,4-dimethyl-1-vinylcyclohex-3-enecarbaldehyde (34 mmol) dropwise at 10° C. The mixture was stirred at room temperature for 1 h and was then cooled to 5° C. A sat. solution of NH$_4$Cl was added dropwise and the mixture was extracted with MTBE (3×50 ml). The combined org. phases were washed with water and brine, dried (MgSO$_4$) and concentrated in vacuo. The residue was purified by chromatography to give (2,4-dimethyl-1-vinylcyclohex-3-enyl)ethanol (53% yield).

Odor description: camphoraceous, woody.

2 Isomers in a ratio of 1:1. $^1$H-NMR (300 MHz, CDCl$_3$): 5.66, 5.61 (2dd, J=17.7, 10.9 Hz, 1H), 5.37-5.35 (m, 1H), 5.22, 5.20 (2d, J=10.9 Hz, 1H), 5.10, 5.09 (2d, J=17.7 Hz, 1H), 3.66, 3.54 (2dq, J=6.8, 6.8 Hz, 1H), 2.46-1.6 (m, 4H), 1.57 (s, 3H), 1.53-1.17 (m, 2H), 1.12, 1.07, 1.01, 0.90 (4d, J=6.8 Hz) ppm. GC/MS (EI): 180 (M$^+$, 2), 162 (18), 147 (15), 136 (40), 121 (70), 107 (100), 93 (61), 82 (72), 67 (43), 55 (22), 41 (20).

EXAMPLE 4

1-(2,4-Dimethyl-1-vinylcyclohex-3-enyl)ethanone

To a solution of (2,4-dimethyl-1-vinylcyclohex-3-enyl) ethanol (20 mmol) in CH$_2$Cl$_2$ (40 ml) at room temperature was added PCC (40 mmol). The mixture was stirred at room temperature over night and was then diluted with hexane, filtered through a pad of celite and concentrated in vacuo. The residue was purified by chromatography to give 1-(2,4-dimethyl-1-vinylcyclohex-3-enyl)ethanone (83% yield).

Odor description: green, floral, woody.

Major (endo) isomer:

$^1$H-NMR (300 MHz, CDCl$_3$): 5.74 (dd, J=10.6, 17.7 Hz, 1H, CH=CH$_2$), 5.34 (bs, 1H, 3-H), 5.29 (d, J=10.6 Hz, 1H, CH=CH$_c$H$_t$), 5.09 (d, J=17.7 Hz, 1H, CH=CH$_c$H$_t$), 2.54-2.43 (m, 1H, 2-H), 2.05 (s, 3H, CH$_3$CO), 1.85-1.60 (m, 4H), 1.58 (s, 3H), 0.81 (d, J=6.8 Hz, 3H) ppm. GC/MS (EI): 178 (M$^+$, 9), 163 (6), 145 (26), 135 (98), 120 (40), 107 (100), 93 (91), 82 (55), 67 (42), 55 (46), 43 (86). IR (neat, v/cm$^{-1}$): 3082 w, 2963 s, 1708 s, 1633 w, 1451 m, 1355 m, 1217 m, 917 m.

EXAMPLE 5

(2,4-Dimethyl-1-vinylcyclohex-3-enyl)methyl acetate

To a solution of (2,4-dimethyl-1-vinylcyclohex-3-enyl) methanol (3.50 g, 21.1 mmol), triethylamine (3.83 g, 38 mmol) and a catalytic amount of DMAP in Et$_2$O (30 ml) was added Ac$_2$O (3.22 g, 31.6 mmol). The mixture was stirred for 5 h, poured on water and extracted with Et$_2$O. The combined organic layers were washed with water and brine, dried and evaporated in vacuo. The residue was distilled bulb-to-bulb to yield (2,4-dimethyl-1-vinylcyclohex-3-enyl)methyl acetate (3.81 g, 86%) as a colorless oil.

Odor description: floral, jasmin, grapefruit $^1$H-NMR (300 MHz, CDCl$_3$): 5.76 (dd, J=10.9, 17.7 Hz, 1H, CH=CH$_2$), 5.18 (bs, 1H, 3-H), 5.07 (d, J=10.9 Hz, 1H, CH=CH$_c$H$_t$), 5.02 (d, J=17.7 Hz, 1H, CH=CH$_c$H$_t$), 4.01 (d, J=10.9 Hz, 1H, CH$_a$H$_b$O), 3.96 (d, J=10.9 Hz, 1H, CH$_a$H$_b$O), 2.22 (bs, 1H, 2-H), 2.01 (s, 3H, CH$_3$O$_2$), 1.91-1.79 (m, 2H), 1.76-1.66 (m, 1H), 1.61 (s, 3H), 1.46-1.37 (m, 1H), 0.88 (d, J=7.5 Hz, 3H) ppm. GC/MS (EI): 208 (M$^+$, 1), 166 (1), 148 (18), 133 (16), 120 (14), 107 (21), 91 (19), 82 (100), 67 (55), 55 (8), 43 (31).

EXAMPLE 6

(2,4-Dimethyl-1-vinylcyclohex-3-enyl)but-3-en-1-ol

In analogy to Example 3, (2,4-dimethyl-1-vinylcyclohex-3-enyl)but-3-en-1-ol (78% yield) was prepared starting from 2,4-dimethyl-1-vinylcyclohex-3-enecarbaldehyde and allylmagnesium chloride.

Odor description: green, floral woody.

2 Isomers in a ratio of 1:1. $^1$H-NMR (300 MHz, CDCl$_3$): 6.00-5.78 (m, 1H), 5.74-5.60 (m, 1H), 5.74-5.60 (m, 1H), 5.36 (bs, 1H), 5.25-5.00 (m, 4H), 3.47-3.38 (m, 1H), 2.54-1.43 (m, 8H), 1.58 (s, 3H), 1.02, 0.92 (2d, J=6.8 Hz, 3H) ppm. GC/MS (EI): 206 (M$^+$, 1), 188 (3), 165 (40), 147 (41), 136 (39), 121 (91), 107 (100), 93 (57), 82 (63), 67 (46), 55 (36), 42 (41).

EXAMPLE 7

(2,4-Dimethyl-1-vinylcyclohex-3-enyl)but-3-en-1-one

Following the general procedure as described in Example 4, (2,4-dimethyl-1-vinylcyclohex-3-enyl)but-3-en-1-one (56% yield) was prepared starting from (2,4-dimethyl-1-vinylcyclohex-3-enyl)but-3-en-1-ol.

Odor description: green, floral, woody.

$^1$H-NMR (300 MHz, CDCl$_3$): 6.00-5.87 (m, 1H), 5.76 (d, J=10.9, 17.7 Hz, 1H), 5.39-5.33 (m, 1H), 5.24 (d, J=10.9 Hz, 1H), 5.13 (d, J=17.7 Hz, 1H), 5.16-5.03 (m, 2H), 3.32-3.31 (m, 2H), 2.60-2.48 (m, 1H), 1.96-1.65 (m, 4H), 1.61 (s, 3H), 0.83 (d, J=6.8 Hz, 3H) ppm. GC/MS (EI): (M$^+$, 2), 189 (3), 163 (29), 145 (19), 135 (100), 120 (32), 107 (83), 93 (73), 79 (36), 69 (40), 55 (34), 41 (54). IR (neat, v/cm$^{-1}$): 3081 m, 2966 s, 1710 s, 1631 m, 1449 m, 1378 w, 1141 m, 917 m.

EXAMPLE 8

2,4-Dimethyl-1-(prop-1-en-2-yl)cyclohex-3-enecarbaldehyde

Following the general procedure as described in Example 1, 2,4-dimethyl-1-(prop-1-en-2-yl)cyclohex-3-enecarbaldehyde (52% yield; boiling point 62-65° C./0.15 mbar) was prepared starting from 2-methyl-penta-1,3-diene and prenal.

Odor description: floral, woody, earthy.

$^1$H-NMR (300 MHz, CDCl$_3$): 9.40 (s, 1H), 5.34 (bs, 1H), 5.15 (s, 1H), 4.89 (s, 1H), 2.75-2.63 (m, 1H), 2.07-1.70 (m, 4H), 1.70 (s, 3H), 1.60 (s, 3H), 1.00 (d, J=7.1 Hz) ppm. $^{13}$C-NMR (75 MHz, CDCl$_3$): 202.8 (d, CHO), 141.8 (s, CH$_2$=CCH$_3$), 133.5 (s, 4-C), 124.9 (d, 3-C), 116.0 (t, CH$_2$=CCH$_3$), 57.6 (s, 1-C), 32.0 (d, 2-C), 27.2 (t, 5-C), 23.2 (q, 4-CH$_3$), 22.8 (t, 6-C), 20.0 (CH$_2$=CCH$_3$), 17.3 (q, 2-CH$_3$) ppm. GC/MS (EI): 178 (M$^+$, 54), 163 (28), 149 (74), 136 (35), 121 (58), 107 (60), 91 (53), 82 (100), 67 (84), 55 (15), 41 (33). IR (neat, v/cm$^{-1}$): 2966 s, 2693 w, 1721 s, 1636 w, 1447 m, 1378 m, 900 m.

EXAMPLE 9

1-(2,4-Dimethyl-1-(prop-1-en-2-yl)cyclohex-3-enyl)ethanol

Following the general procedure described in Example 3, 1-(2,4-dimethyl-1-(prop-1-en-2-yl)cyclohex-3-enyl)ethanol was prepared in 92% yield starting from 2,4-dimethyl-1-(prop-1-en-2-yl)cyclohex-3-enecarbaldehyde.

Odor description: fresh, green, woody.

Mixture of 2 isomers in a ratio of 6:4. $^1$H-NMR (300 MHz, CDCl$_3$): 5.45-5.37 (m, 1H), 5.18, 5.12 (2 s, 1H), 4.84, 4.77 (2 s, 1H), 3.74, 3.57 (2dq, J$_1$=6.4, 6.4 Hz, J$_2$=11.0, 6.4 Hz, 1H), 2.76-2.66, 2.48-2.39 (2 m, 1H), 2.07-1.23 (m, 4H), 1.84 (s, 3H), 1.59 (s, 3H), 1.14, 1.09 (2 d, J=6.4 Hz, 3H), 1.06, 0.95 (2 s, J=6.4 Hz, 3H) ppm. GC/MS (EI): 194 (M$^+$, 1), 176 (10), 161 (15), 150 (31), 135 (100), 121 (45), 107 (98), 91 (47), 82 (32), 67 (27), 55 (16), 41 (29). IR (neat, v/cm$^{-1}$): 3437br, 3085 w, 2964 s, 1631 w, 1451 m, 1373 m, 833 m.

EXAMPLE 10

1-(2,4-Dimethyl-1-(prop-1-en-2-yl)cyclohex-3-enyl) ethyl acetate

In analogy to Example 5, 1-(2,4-dimethyl-1-(prop-1-en-2-yl)cyclohex-3-enyl)ethyl acetate was prepared starting from 1-(2,4-dimethyl-1-(prop-1-en-2-yl)cyclohex-3-enyl)ethanol.

Odor description: floral, spicy, eugenol

Mixture of 2 isomers in a ratio of 6:4. $^1$H-NMR (300 MHz, CDCl$_3$): 5.41-5.36, 5.32-5.28 (2 m, 1H), 5.12, 5.10 (2 s, 1H), 4.84, 4.77 (2 s, 1H), 5.01, 4.86 (2q, J$_1$=6.4 Hz, J$_2$=6.4 Hz, 1H), 2.64-2.55, 2.48-2.38 (2 m, 1H), 2.06, 2.04 (2 s, 3H), 2.00-1.44 (m, 4H), 1.87, 1.84 (2 s, 3H), 1.59, 1.58 (2 s, 3H), 1.14, 1.10, 0.99, 0.93 (4 d, J=6.4 Hz, 6H) ppm. GC/MS (EI): 236 (M$^+$, 1), 194 (1), 176 (37), 161 (76), 147 (24), 134 (49), 119 (75), 107 (89), 91 (46), 82 (55). IR (neat, v/cm$^{-1}$): 2963 s, 1738 s, 1633 m, 1451 m, 1374 m, 1247 s.

EXAMPLE 11

1-(2,4-Dimethyl-1-(prop-1-en-2-yl)cyclohex-3-enyl)-2-methylpropan-1-ol

To a mixture of Mg (1.2 g, 50 mmol), Li (0.35 g, 50 mmol) and 2,4-dimethyl-1-(prop-1-en-2-yl)cyclohex-3-enecarbaldehyde (8.9 g, 50 mmol) was added 2-bromopropane (7.5 g, 60 mmol). The mixture was stirred for 24 h under an argon atmosphere and was then poured on ice-cold sat. NH$_4$Cl solution. The mixture was extracted with MTBE (3×50 ml). The combined org. phases were washed with water and brine, dried (MgSO$_4$) and concentrated in vacuo. The residue was distilled in a Kugelrohr oven to yield 8.0 (72%) of a colorless oil.

Odor description: fruity, green, grapefruit, powerful.

$^1$H-NMR (300 MHz, CDCl$_3$): 5.38 (bs, 1H), 5.11, 4.99 (2 s, 1H), 4.93, 4.85 (2 s, 1H), 3.30-3.22 (m, 1H), 2.74-2.65, 2.58-2.50 (2 m, 1H), 2.23-2.47 (m, 5H), 1.85, 1.83 (2 s, 3H), 1.58 (s, 3H), 1.05, 1.01, 0.99, 0.93, 0.86, 0.77 (6 d, J=6.8 Hz, 9H) ppm. GC/MS (EI): 222 (M$^+$, 1), 204 (1), 189 (1), 179 (3) 161 (6), 150 (29), 135 (100), 122 (53), 107 (66), 93 (26), 82 (18), 67 (15), 55 (12), 41 (24). IR (neat, v/cm$^{-1}$): 3501br, 2962 s, 1453 m, 1374 m, 1003 m, 888 m.

EXAMPLE 12

1-(2,4-Dimethyl-1-(prop-1-en-2-yl)cyclohex-3-enyl)-2-methylpropan-1-one

Following the general procedure as described in Example 4, 1-(2,4-dimethyl-1-(prop-1-en-2-yl)cyclohex-3-enyl)-2-methylpropan-1-one was prepared (75% yield) starting from 1-(2,4-dimethyl-1-(prop-1-en-2-yl)cyclohex-3-enyl)-2-methylpropan-1-ol.

Odor description: fruity, grapefruit, woody.

Major (endo) isomer:

$^1$H-NMR (300 MHz, CDCl$_3$): 5.34-5.31 (m, 1H), 5.15 (s, 1H), 5.04 (s, 1H), 2.99 (sept, J=6.8 Hz, 1H), 2.87-2.75 (m, 1H), 1.94-1.70 (m, 4H), 1.66 (s, 3H), 1.57 (s, 3H), 1.04 (d, J=6.8 Hz, 3H), 1.00 (d, J=6.8 Hz, 3H), 0.85 (d, J=6.8 Hz, 3H) ppm. $^{13}$C-NMR (75 MHz, CDCl$_3$): 217.5 (s), 142.5 (s), 132.3 (s), 125.0 (d), 115.8 (t), 60.3 (s), 35.3 (d), 32.9 (d), 27.4 (t), 23.1 (q), 22.3 (q), 21.5 (t), 20.7 (q), 20.1 (q), 18.7 (q) ppm. GC/MS (EI): 220 (M$^+$, 2), 205 (3), 187 (11), 177 (10), 159 (43), 149 (73), 121 (77), 107 (100), 91 (48), 71 (54), 55 (14), 43 (78). IR (neat, v/cm$^{-1}$): 2969 s, 1705 s, 1637 m, 1447 s, 1379 m, 896 m.

EXAMPLE 13

1-(2,4-Dimethyl-1-(prop-1-en-2-yl)cyclohex-3-enyl) ethanone

Following the general procedure described in Example 4, 1-(2,4-dimethyl-1-(prop-1-en-2-yl)cyclohex-3-enyl)ethanone (70% yield) was prepared starting from 1-(2,4-dimethyl-1-(prop-1-en-2-yl)cyclohex-3-enyl)ethanol.

Odor description: green, fruity, woody.

$^1$H-NMR (300 MHz, CDCl$_3$): 5.33-5.28 (m, 1H), 5.10 (s, 1H), 5.00 (s, 1H), 2.71-2.61 (m, 1H), 2.02 (s, 3H), 1.91-1.62 (m, 4H), 1.62 (s, 3H), 1.56 (s, 3H), 0.82 (s, J=6.7 Hz, 3H) ppm. GC/MS (EI): 192 (M$^+$, 7), 177 (14), 150 (56), 135 (47), 121 (82), 107 (100), 91 (51), 83 (29), 77 (24), 67 (22), 55 (15), 43 (56). IR (neat, v/cm$^{-1}$): 3091 w, 2964 s, 1708 s, 1639 m, 1446 s, 1378 m, 1354 m, 1211 m, 1155 m, 898 m.

EXAMPLE 14

1-(2,4-Dimethyl-1-(prop-1-en-2-yl)cyclohex-3-enyl) but-3-en-1-ol

In analogy to Example 3, 1-(2,4-dimethyl-1-(prop-1-en-2-yl)cyclohex-3-enyl)but-3-en-1-ol (91% yield) was prepared starting from 2,4-dimethyl-1-(prop-1-en-2-yl)cyclohex-3-enecarbaldehyde and allylmagnesium chloride Odor description: fruity, fresh, woody.

Mixture of 4 isomers. $^1$H-NMR (300 MHz, CDCl$_3$) 6.00-5.78 (m, 1H), 5.53-5.36 (m, 1H), 5.17-4.71 (m, 4H), 3.52-3.38 (m, 1H), 2.81-1.50 (m, 7H), 1.85, 1.83 (4s, 3H), 1.65, 1.64, 1.59, 1.58 (4s, 3H), 1.06, 0.96, 0.85, 0.80 (4d, J=6.8 Hz, 3H) ppm. GC/MS (EI): major isomer: 220 (M$^+$, 1), 202 (1), 179 (12), 161 (17), 150 (25), 135 (100), 121 (43), 107 (87), 93 (40), 91 (39), 82 (22), 67 (25), 55 (17), 41 (45). IR (neat, v/cm$^{-1}$): 3487br, 3079 m, 2962 s, 1449 m, 992 m, 910 m.

EXAMPLE 15

1-(2,4-Dimethyl-1-(prop-1-en-2-yl)cyclohex-3-enyl) but-3-en-1-one

Following the general procedure described in Example 4, 1-(2,4-dimethyl-1-(prop-1-en-2-yl)cyclohex-3-enyl)but-3-en-1-one was prepared starting from 1-(2,4-dimethyl-1-(prop-1-en-2-yl)cyclohex-3-enyl)but-3-en-1-ol as a mixture of 2 isomers in a ratio of 8:2.

Odor description: fruity, peppery, fresh, woody.

$^1$H-NMR (300 MHz, CDCl$_3$): 6.03-5.88 (m, 1H), 5.47-5.31 (m, 1H), 5.15-5.02 (m, 4H), 3.24-3.15 (m, 2H), 2.85-2.65 (m, 1H), 2.13-1.56 (m, 4H), 1.64 (s, 3H), 1.59 (s, 3H), 0.83, 0.73 (2d, J=6.8 Hz, 3H) ppm. GC/MS (EI): 218 (M$^+$, 5), 203 (5), 177 (26), 159 (17), 149 (77), 135 (36), 121 (82), 107

(100), 91 (42), 69 (38), 41 (52). IR (neat, v/cm$^{-1}$); 2962 s, 1710 s, 1631 s, 1446 m, 1139 w, 897 m.

EXAMPLE 16

1-(2,4-Dimethyl-1-(prop-1-en-2-yl)cyclohex-3-enyl)but-2-en-1-one

A solution of 1-(2,4-dimethyl-1-(prop-1-en-2-yl)cyclohex-3-enyl)but-3-en-1-one (2.5 g, 11.5 mmol) and triethylamine (2 g) in CH$_2$Cl$_2$ was stirred at room temperature over night. The solvent and excess of triethylamine were evaporated and the residue distilled bulb-to-bulb to yield the title compound (80%) as a slightly yellow oil.

Odor description: spicy, black pepper, damascone, fruity.

Mixture of 4 isomers, major isomer: $^1$H-NMR (300 MHz, CDCl$_3$): 6.94 (dq, J=15.5, 7.1 Hz, 1H), 6.37 (d, J=15.5 Hz, 1H), 5.31 (bs, 1H), 5.12 (s, 1H), 5.03 (s, 1H), 2.68-2.55 (m, 1H), 1.85-1.53 (m, 13H), 0.80 (d, J=7.1 Hz, 3H) ppm. $^{13}$C-NMR (75 MHz, CDCl$_3$): 201.2 (s), 143.0 (s), 141.9 (d), 132.6 (s), 127.0 (d), 124.6 (d), 115.1 (t), 58.2 (s), 32.8 (d), 27.3 (t), 23.2 (q), 21.1 (t), 19.9 (q), 18.2 (q), 18.1 (q) ppm. GC/MS (EI): 218 (M$^+$, 5), 203 (8), 176 (24), 133 (57), 121 (59), 107 (72), 91 (37), 69 (100), 41 (49). IR (neat, v/cm$^{-1}$): 3089 m, 2968 s, 1696 s, 1631 s, 1445 s, 1377 m, 1142 m, 895 s.

EXAMPLE 17

1-(Buta-1,3-dienyl)-2,4-dimethylcyclohex-3-enecarbaldehyde

Following the general procedure as described in Example 1, the title compound was prepared (50% yield) starting from 2-methyl-penta-1,3-diene and sorbic aldehyde.

Odor description: fruity, apple, mild floral

4 Isomers In a ratio of 9:5:2:1. $^1$H-NMR (300 MHz, CDCl$_3$): 9.62, 9.51, 9.47, 9.39 (4 s, 1H), 6.44-6.01 (m, 2H), 5.63-5.05 (m, 4H), 2.62-2.40 (m, 1H), 1.95-1.60 (m, 7H), 0.99, 0.98, 0.92, 0.91 (4d, J=7.1 Hz, 3H) ppm. Major isomer: $^{13}$C-NMR (75 MHz, CDCl$_3$): 202.1 (d), 136.7 (d), 134.1 (s), 134.0 (d), 133.3 (d), 124.6 (d), 117.4 (t), 53.6 (s), 35.2 (d), 27.1 (t), 25.0 (t), 23.3 (q), 17.16 (q) ppm. GC/MS (EI): 190 (M$^+$, 37). 175 (5), 161 (16), 147 (12), 133 (12), 119 (27), 105 (40), 91 (45), 82 (100), 67 (65), 55 (13), 41 (20). IR (neat, v/cm$^{-1}$): 2963 s, 2710 m, 1718 s, 1449 m, 1378 m, 1006 m, 907 m.

EXAMPLE 18

3,4-Dimethyl-1-vinylcyclohex-3-enecarbaldehyde

Following the general procedure described in Example 1, the title compound was prepared starting from 2,3-dimethyl-buta-1,3-diene and crotonic aldehyde.

Odor description: fresh, green, terpenic, fruity, camphoraceous $^1$H-NMR (300 MHz, CDCl$_3$): 9.33 (s, 1H), 5.67 (dd, J=17.6, 10.5 Hz, 1H), 5.23 (d, J=10.5 Hz, 1H), 5.09 (d, J=17.6 Hz, 1H), 2.36-1.60 (m, 6H), 1.66 (s, 3H), 1.57 (s, 3H) ppm. $^{13}$C-NMR (75 MHz, CDCl$_3$): 202.1 (d), 138.1 (d), 125.7 (s), 122.8 (s), 116.7 (t), 52.4 (t), 35.8 (t), 28.4 (t), 27.6 (t), 19.2 (q), 18.8 (q) ppm. GC/MS (EI): 164 (M$^+$, 32), 149 (23), 135 (71), 121 (42), 107 (93), 91 (100), 79 (86), 67 (80), 55 (41), 41 (56). IR (neat, v/cm$^{-1}$): 2920 s, 1729 s, 1441 m, 997 w, 921 m.

EXAMPLE 19

2-Methyl-1-(2-methylprop-1-enyl)cyclohex-3-enecarbaldehyde

Following the general procedure described in Example 1, the title compound was prepared starting from penta-1,3-diene and 4-methyl-pent-2-enal.

EXAMPLE 20

2,4-Dimethyl-1-(2-methylprop-1-enyl)cyclohex-3-enecarbaldehyde

Following the general procedure described in Example 1, the title compound was prepared starting from 2-methyl-penta-1,3-diene and 4-methyl-pent-2-enal. 2 Isomers in a ratio of 9:1.

Odor description: fruity, apple, rose-petal, watery $^1$H-NMR (300 MHz, CDCl$_3$): 9.41 (s, 1H), 5.28 (s, 1H), 4.95 (s, 1H), 2.34-2.24 (m, 1H), 1.90-1.70 (m, 4H), 1.71 (s, 3H), 1.61 (s, 3H), 1.49 (s, 3H), 0.85 (d, J=7.1 Hz, 3H) ppm. $^{13}$C-NMR (75 MHz, CDCl$_3$): 203.3 (d), 137.6 (s), 134.6 (s), 124.8 (d), 124.1 (d), 52.9 (s), 36.9 (d), 27.4 (t), 27.1 (q), 23.3 (q), 21.9 (t), 18.6 (q), 17.3 (q) ppm. GC/MS (EI): 192 (M$^+$, 63), 177 (21), 163 (31), 135 (19), 121 (27), 107 (69), 95 (35), 82 (100), 67 (46), 55 (14), 41 (23). IR (neat, v/cm$^{-1}$): 2912 s, 2712 m, 1721 s, 1449 m, 1378 m, 821 w.

EXAMPLE 21

1-(2,4-Dimethyl-1-(2-methylprop-1-enyl)cyclohex-3-enyl)ethanol

Following the general procedure described in Example 3, the title compound was prepared starting from 2,4-dimethyl-1-(2-methylprop-1-enyl)cyclohex-3-enecarbaldehyde. 2 Isomers in the ratio of 1:1.

Odor description: earthy, dry woody, camphoraceous $^1$H-NMR (300 MHz, CDCl$_3$): 5.33-5.20 (m, 1H), 4.81, 4.76 (2bs, 1H), 2.80-3.70, 3.61-3.52 (2m, 1H), 2.41-2.31 (m, 1H), 1.84, 1.76, 1.75, 1.73, 1.60, 1.60 (6 s, 9H), 2.01-1.39 (m, 5H), 1.18, 1.10 (2 d, J=6.4 Hz, 3H), 1.00, 0.87 (2 d, J=7.2 Hz, 3H) ppm. GC/MS (EI): 208 (M$^+$, 5), 190 (4), 175 (5), 163 (61), 135 (20), 121 (42), 107 (100), 93 (52), 83 (34), 69 (30), 55 (23), 41 (22). IR (neat, v/cm$^{-1}$): 3422br, 2967 s, 1451 m, 1374 m, 1102 m.

EXAMPLE 22

1-Cyclopentenyl-2,4-dimentylcyclohex-3-enecarbaldehyde

Following the general procedure described in Example 1, the title compound was prepared (20%) starting from 2-methylpenta-1,3-diene and 2-cyclopentylidene-acetaldehyde. 2 isomers in a ratio of 8:2.

Odor description: muguet, fruity

Major isomer: $^1$H-NMR (300 MHz, CDCl$_3$): 9.40 (s, 1H), 5.58 (s, 1H), 5.33 (s, 1H), 2.67 (bs, 1H), 2.36-1.70 (m, 10H), 1.60 (s, 3H), 0.98 (d, J=6.9 Hz, 3H) ppm. $^{13}$C-NMR (75 MHz, CDCl$_3$): 202.2 (d), 141.5 (s), 133.4 (s), 129.5 (d), 125.0 (d), 54.6 (s), 33.0 (d), 32.8 (t), 32.0 (t), 27.3 (t), 23.3 (q), 23.2 (2 t), 17.3 (q) ppm. GC/MS (EI): 204 (M$^+$, 30), 189 (4), 175 (10), 147 (19), 133 (10), 119 (14), 105 (20), 91 (31), 82 (100), 67 (49), 55 (10), 41 (23).

EXAMPLE 23

4,5-Dimethyl-2-(2-methylprop-1-enyl)-1-vinylcyclohex-3-enecarbaldehyde

Following the general procedure described in Example 1, the title compound was prepared starting from alloocimene and crotonic aldehyde. (2 isomers in a ratio of 85:15.

Odor description: slightly fruity, green, weak

Major isomer: $^1$H-NMR (300 MHz, CDCl$_3$): 9.13 (s, 1H), 5.70-5.59 (m, 1H), 5.24-4.76 (m, 4H), 3.32-3.19 (m, 1H), 2.12-1.15 (m, 4H), 1.63, 1.59, 1.59 (3 s, 9H), 0.99 (d, J=6.8 Hz, 3H) ppm. $^{13}$C-NMR (75 MHz, CDCl$_3$): 201.4 (d), 138.2 (s), 137.9 (d), 133.6 (s), 123.7 (d), 121.5 (d), 118.0 (t), 55.4 (s), 38.8 (d), 32.7 (t), 30.6 (d), 25.9 (q), 21.1 (q), 19.3 (q), 18.3 (q) ppm. GC/MS (EI): 218 (M$^+$, 4), 203 (1), 189 (2), 175 (1), 161 (1), 147 (3), 136 (56), 121 (100), 105 (12), 91 (12), 77 (6), 67 (2), 55 (4), 41 (5). IR (neat, v/cm$^{-1}$): 2967 s, 1725 s, 1445 m, 1377 m, 921 w.

EXAMPLE 24

2-Methyl-4-(4-methylpent-3-enyl)-1-vinylcyclohex-3-enecarbaldehyde

Following the general procedure described in Example 1, the title compound was prepared (50% yield) starting from 2-methyl-6-methylenenona-2,7-diene and crotonic aldehyde.

Odor description: muguet, fruity.

(Endo:exo-isomers in a ratio of 8:2). Endo-isomer: $^1$H-NMR (300 MHz, CDCl$_3$): 9.49 (s, 1H), 5.76 (dd, J=17.7, 10.9 Hz, 1H), 5.37-5.33 (m, 2H), 5.27 (d, J=10.9 Hz, 1H), 5.08 (d, J=17.7 Hz, 1H), 2.55-2.43 (m, 1H), 2.09-2.65 (m, 8H), 1.67 (s, 3H), 1.58 (s, 3H), 1.00 (d, J=7.1 Hz, 3H) ppm. $^{13}$C-NMR (75 MHz, CDCl$_3$): 203.0 (d), 138.3 (d), 137.5 (s), 131.4 (s), 124.4 (d), 124.0 (d), 117.4 (t), 54.3 (s), 37.3 (t), 34.7 (d), 26.4 (t), 25.7 (q), 25.3 (t), 25.0 (t), 17.7 (q), 17.2 (q) ppm. GC/MS (EI): 232 (M$^+$, 5), 217 (6), 203 (14), 189 (12), 171 (6), 150 (22), 135 (20), 119 (23), 107 (100), 91 (35), 79 (30), 69 (92), 55 (28), 41 (68).

EXAMPLE 25

4-Methyl-1-vinyl-cyclohex-3-enecarbaldehyde, 3-methyl-1-vinyl-cyclohex-3-ene-carbaldehyde and Perilla aldehyde (ratio 5.5:3:1.5)

Following the general procedure described in Example 1, a mixture of 4-methyl-1-vinyl-cyclohex-3-enecarbaldehyde, 3-methyl-1-vinyl-cyclohex-3-ene-carbaldehyde and Perilla aldehyde (ratio 5.5:3:1.5) was obtained (yield 31%) starting from isoprene and crotonic aldehyde. The components were separated by chromatography (eluent hexane:MTBE 50:1 to 10:1). The analytical data of racemic Perilla aldehyde obtained this way were identical with those of an authentic sample.

Odor description of the mixture: powerful, fresh green, fruity, spicy.

4-Methyl-1-vinyl-cyclohex-3-enecarbaldehyde: $^1$H-NMR (300 MHz, CDCl$_3$): 9.35 (s, 1H), 5.69 (dd, J=17.7, 10.7 Hz, 1H), 5.40 (bs, 1H), 5.26 (d, J=10.7 Hz, 1H), 5.13 (d, J=17.7 Hz, 1H), 2.44 (bs, 1H), 2.41 (bs, 1H), 2.10-1.64 (m, 5H), 1.63 (s, 3H) ppm. $^{13}$C-NMR (75 MHz, CDCl$_3$): 202.0 (d), 138 (d), 134.4 (s), 118.0 (d), 116.9 (t), 51.4 (s), 29.8 (t), 27.3 (t), 26.9 (t), 22.0 (q) ppm. GC/MS (EI): 150 (M$^+$, 23), 135 (24), 121 (45), 107 (33), 93 (100), 79 (98), 67 (54), 55 (37), 39 (38).

3-Methyl-1-vinyl-cyclohex-3-enecarbaldehyde: $^1$H-NMR (300 MHz, CDCl$_3$): 9.36 (s, 1H), 5.71 (dd, J=10.7, 17.7 Hz, 1H), 5.37 (bs, 1H), 5.27 (d, J=10.7 Hz, 1H), 5.12 (d, J=17.7 Hz, 1H), 2.37 (bs, 1H), 2.33 (bs, 1H), 2.10-1.64 (m, 5H), 1.72 (s, 3H) ppm. $^{13}$C-NMR (75 MHz, CDCl$_3$): 201.7 (d), 137.9 (d), 131.2 (s), 120.9 (d), 116.8 (t), 52.2 (s), 34.1 (t), 26.7 (t), 23.6 (q), 22.2 (t) ppm. GC/MS (EI): 150 (M$^+$, 10), 135 (16), 121 (78), 107 (29), 93 (100), 79 (88), 67 (32), 55 (31), 39 (32). IR (neat, v/cm$^{-1}$): 2917 s, 2854 m, 2707 w, 1726 s, 1632 w, 1439 m, 921 m.

EXAMPLE 26

4-Methyl-1-vinyl-cyclohex-3-enecarbaldehyde oxime, 3-methyl-1-vinyl-cyclohex-3-ene-carbaldehyde oxime (ratio 6:4)

A solution of a mixture of 4-methyl-1-vinyl-cyclohex-3-enecarbaldehyde and 3-methyl-1-vinyl-cyclohex-3-ene-carbaldehyde (6:4, 1.5 g, 10 mmol), hydroxylamine hydrochloride (1.04 g, 15 mmol) and NaHCO$_3$ (1.26 g, 15 mmol) in EtOH/Water (20 ml, 3:1) was stirred at 50° C. for 4 h. The mixture was diluted with water and extracted 3 times with MTBE. The combined org. layers were washed with water and brine, dried (MgSO$_4$) and evaporated in vacuo. 4-Methyl-1-vinyl-cyclohex-3-enecarbaldehyde oxime and 3-methyl-1-vinyl-cyclohex-3-ene-carbaldehyde oxime was obtained after bulb-to-bulb distillation (ratio 6:4, yield 70%) as a colorless oil.

Odor description of the mixture: floral, violet leaf, green $^1$H-NMR (300 MHz, CDCl$_3$): 8.43, 8.35 (2 bs, 1H), 7.32 (s, 1H), 5.82 (dd, J=17.7, 10.6 Hz, 1H), 5.38 (bs, 1H), 5.14-5.01 (m, 2H), 2.28-1.64 (m, 6H), 1.70, 1.65 (2 s, 3H) ppm. GC/MS (EI): 165 (M$^+$, 2), 148 (24), 131 (24), 120 (25), 105 (100), 91 (44), 79 (30), 68 (96), 53 (28), 39 (25). IR (neat, v/cm$^{-1}$): 3315 br, 2927 s, 1635 m, 1439 s, 922 s.

EXAMPLE 27

1-(Prop-1-en-2-yl)cyclohex-3-enecarbaldehyde

Following the general procedure as described in Example 1, the title compound was prepared (31% yield) starting from 1,3-butadiene and prenal.

Odor description: fresh, green, camphoraceous, *perilla* aldehyde-like $^1$H-NMR (300 MHz, CDCl$_3$): 9.23 (s, 1H), 5.72-5.60 (m, 2H), 5.07 (s, 1H), 4.91 (s, 1H), 2.54-2.44 (m, 1H), 2.18-2.71 (m, 5H), 1.68 (s, 3H) ppm. $^{13}$C-NMR (75 MHz, CDCl$_3$): 201.4 (d), 143.0 (s), 126.8 (d), 124.4 (d), 114.4 (t), 54.4 (s), 29.0 (t), 25.5 (t), 22.4 (t), 19.5 (q) ppm. GC/MS (EI): 150 (M$^+$, 9), 135 (17), 121 (36), 107 (21), 93 (73), 79 (100), 67 (21), 55 (24), 41 (27). IR (neat, v/cm$^{-1}$): 3028 w, 2923 s, 2698 m, 1725 s, 1668 m, 1634 m, 1440 m, 1377 m, 901 m,

EXAMPLE 28

1-(But-1-enyl)-2,4-dimethylcyclohex-3-enecarbaldehyde

Following the general procedure described in Example 1, the title compound (71% yield) was prepared starting from 2-methyl-penta-1,3-diene and 2-hexenal.

Odor description: fruity, apple-like, floral.

4 isomers in a ratio of 5:2:7:1. $^1$H-NMR (300 MHz, CDCl$_3$): 9.62, 9.53, 9.45, 9.36 (4s, 1H), 5.60-5.14 (m, 3H), 2.63-2.33 (m, 1H), 2.13-1.61 (m, 9H), 1.01-0.90 (m, 6H) ppm. $^{13}$C-NMR (75 MHz, CDCl$_3$): Major isomer: 203.3 (d), 137.3 (d), 134.6 (s), 129.0 (d), 124.1 (d), 53.3 (s), 36.6 (d), 27.3 (t), 27.1 (t), 23.3 (q), 22.7 (t), 17.2 (q), 14.1 (q) ppm. GC/MS (EI): 192 (M$^+$, 20), 163 (20), 135 (13), 121 (16), 107 (35), 93 (24), 82 (100), 67 (46), 55 (18), 41 (20). IR (neat, v/cm$^{-1}$): 1964 s, 2874 m, 2711 w, 1721 s, 1451 m.

EXAMPLE 29

4-Methyl-1-(prop-1-en-2-yl)cyclohex-3-enecarbaldehyde and 3-methyl-1-(prop-1-en-2-yl)cyclohex-3-enecarbaldehyde Following the general procedure described in Example 1, a mixture of 4-methyl-1-(prop-1-en-2-yl)cyclohex-3-enecarbaldehyde and 3-methyl-1-(prop-1-en-2-yl)cyclohex-3-enecarbaldehyde (31% yield) was prepared starting from isoprene and prenal.

Odor description: green, fruity, mango, damascone, plum.

Mixture of isomers in a ratio of 6:4. $^1$H-NMR (300 MHz, CDCl$_3$): 9.22, 9.21 (2s, 1H), 5.04-4.83 (m, 3H), 2.51-2.33 (m, 2H), 2.17-1.72 (m, 5H), 1.70, 1.68, 1.67, 1.60 (4 s, 6H) ppm. 4-methyl-1-(prop-1-en-2-yl)cyclohex-3-enecarbaldehyde: $^{13}$C-NMR (75 MHz, CDCl$_3$): 201.7 (d), 143.0 (s), 134.0 (s), 118.4 (d), 114.4 (t), 54.2 (s), 29.3 (t), 27.2 (t), 26.0 (t), 23.2 (q), 19.6 (q) ppm. GC/MS (EI): 164 (M$^+$, 20), 149 (31), 135 (68), 121 (35), 107 (71), 93 (100), 79 (64), 67 (40), 55 (28), 41 (38). 3-Methyl-1-(prop-1-en-2-yl)cyclohex-3-enecarbaldehyde: $^{13}$C-NMR (75 MHz, CDCl$_3$): 201.5 (d), 143.0 (s), 131.6 (s), 120.6 (d), 114.3 (t), 55.0 (s), 33.7 (t), 25.4 (t), 23.6 (q), 22.4 (t), 19.6 (q) ppm. GC/MS (EI): 164 (M$^+$, 18), 149 (32), 135 (68), 121 (34), 107 (72), 93 (100), 79 (64), 67 (41), 55 (27), 41 (38). IR (neat, v/cm$^{-1}$): 2967 m, 2921 s, 1726 s, 1635 m, 1441 m, 1377 m, 899 m.

EXAMPLE 30

1-Vinylcyclohex-3-ene carbaldehyde and 4-vinylcyclohex-1-ene carbaldehyde

Following the general procedure described in Example 1, a mixture of 1-vinylcyclohex-3-ene carbaldehyde and 4-vinylcyclohex-1-ene carbaldehyde (42% yield) was prepared starting from 1,3-butadiene and crotonic aldehyde.

Odor description of the mixture: green, fruity, apple, melon, floral, violet.

1-Vinylcyclohex-3-ene carbaldehyd: $^1$H-NMR (300 MHz, CDCl$_3$): 9.38 (s, 1H), 5.77-5.63 (m, 3H), 5.29 (d, J=10.6 Hz, 1H), 5.16 (d, J=17.7 Hz, 1H), 2.53-1.67 (m, 6H) ppm. $^{13}$C-NMR (75 MHz, CDCl$_3$): 201.8 (d), 137.9 (d), 127.1 (d), 123.9 (d), 117.0 (t), 51.7 (s), 29.4 (t), 26.9 (t), 22.0 (t) ppm. GC/MS (EI): 136 (W, 5), 118 (17), 107 (28), 91 (46), 79 (100), 67 (9), 53 (14), 39 (23).

4-Vinylcyclohex-1-ene carbaldehyde: $^1$H-NMR (300 MHz, CDCl$_3$): 9.41 (s, 1H), 6.79 (bs, 1H), 5.81 (ddd, J=17.0, 10.2, 6.6 Hz, 1H), 5.04 (d, J=17.0 Hz, 1H), 4.99 (d, J=10.2 Hz, 1H), 2.55-2.05 (m, 5H), 1.91-1.83 (m, 1H), 1.44-1.30 (m, 1H) ppm. $^{13}$C-NMR (75 MHz, CDCl$_3$): 194.0 (d), 150.1 (d), 142.0 (d), 141.3 (s), 113.5 (t), 37.1 (d), 32.0 (t), 27.2 (t), 20.8 (t) ppm. GC/MS (EI): 136 (M$^+$, 21), 121 (14), 107 (60), 91 (41), 79 (88), 67 (27), 54 (100), 39 (49). IR (neat, v/cm$^{-1}$): 2928 s, 1686 s, 1643 m, 1420 w, 1178 w, 916 w.

EXAMPLE 31

(4-Vinylcyclohex-1-enyl)methanol

Following the general procedure as described in Example 2, the title compound (85% yield) was prepared starting from 4-vinylcyclohex-1-ene carbaldehyde.

Odor description: spicy, cinnamon, rosy, fruity, green.

$^1$H-NMR (300 MHz, CDCl$_3$): 5.48 (ddd, J=17.0, 10.2, 6.4 Hz, 1H), 5.68 (bs, 1H), 5.03 (d, J=17.0 Hz, 1H), 4.96 (d, J=10.2 Hz, 1H), 4.00 (s, 2H), 2.27-1.81 (m, 6H), 1.60 (bs, OH), 1.48-1.35 (m, 1H) ppm. GC/MS (EI): 138 (M$^+$, 9), 120 (26), 105 (58), 91 (64), 79 (100), 67 (33), 55 (57), 41 (35). IR (neat, v/cm$^{-1}$): 3332br, 3079 m, 2914 s, 1640 m,

EXAMPLE 32

1-(4-Vinylcyclohex-1-enyl) ethanol

Following the general procedure as described in Example 3, the title compound (66% yield) was prepared starting from 4-vinylcyclohex-1-ene carbaldehyde.

Odor description: cinnamic, fruity, apple, green

Mixture of 2 isomers in the ratio of 1:1. $^1$H-NMR (300 MHz, CDCl$_3$): 5.92-5.80 (m, 1H), 5.66 (bs, 1H), 5.05-4.93 (m, 2H), 4.24-4.12 (m, 1H), 2.32-1.79 (m, 6H), 1.48-1.31 (m, 1H), 1.25 (2d, J=6.5 Hz, 3H) ppm. GC/MS (EI): major isomer: 152 (M$^+$, 9), 134 (35), 119 (33), 105 (53), 91 (60), 79 (100), 67 (34), 55 (24), 43 (68). IR (neat, v/cm$^{-1}$): 3369br, 3080 m, 2973 m, 2925 s, 1436 m, 1071 m, 912 m.

EXAMPLE 33

2-Methyl-4-vinylcyclohex-1-ene carbaldehyde

Following the general procedure described in Example 1, the title compound (12% yield) was prepared starting from 1,3-butadiene and prenal.

Odor description: green, fruity, cinnamon.

$^1$H-NMR (300 MHz, CDCl$_3$): 10.12 (s, 1H), 5.79 (ddd, J=17.0, 10.2, 6.1 Hz, 1H), 5.06-4.95 (m, 2H), 2.48-1.22 (m, 7H), 2.14 (s, 3H) ppm. $^{13}$C-NMR (75 MHz, CDCl$_3$): 191.0 (d), 155.2 (s), 142.2 (d), 133.3 (s), 113.4 (t), 39.2 (t), 37.0 (d), 27.5 (t), 21.9 (t), 18.3 (q) ppm. GC/MS (EI): 150 (M$^+$, 42), 135 (45), 121 (47), 107 (55), 93 (87), 79 (100), 67 (94), 54 (57), 41 (54). IR (neat, v/cm$^{-1}$): 2921 s, 1714 s, 1666 s, 1440 m, 1379 m, 1244 m, 914 m.

EXAMPLE 34

(2-Methyl-4-vinylcyclohex-1-enyl)methanol

Following the general procedure described in Example 2, the title compound (92% yield) was prepared starting from 2-methyl-4-vinylcyclohex-1-ene carbaldehyde.

Odor description: metallic, floral, rosy.

$^1$H-NMR (300 MHz, CDCl$_3$): 5.82 (ddd, J=17.0, 10.2, 6.4 Hz, 1H), 5.01 (d, J=17.0 Hz, 1H), 4.95 (d, J=10.2 Hz, 1H), 4.16 (d, J=10.9 Hz, 1H), 4.07 (d, J=10.9 Hz, 1H), 2.26-1.92 (m, 7H), 1.71 (s, 3H) ppm. GC/MS (EI): 152 (M$^+$, 7), 134

(43), 119 (77), 93 (100), 91 (98), 79 (94), 69 (43), 55 (36), 41 (54). IR (neat, v/cm$^{-1}$): 3349br, 3079 w, 2920 s, 1640 w, 1436 s, 995 s, 910 m.

EXAMPLE 35

3a,4,7,7a-Tetrahydro-1H-indene-6-carbaldehyde

Following the general procedure described in Example 1, the title compound (40% yield; boiling point: 65-70° C./0.54 mbar) was prepared starting from cyclopentadiene and crotonic aldehyde.

Odor description: green, melon, cucumber, apple, marine, floral.

$^1$H-NMR (300 MHz, CDCl$_3$): 9.40 (s, 1H), 6.93 (dd, J=4.9, 4.9 Hz, 1H), 5.65-5.53 (m, 2H), 2.99-2.91 (m, 1H), 2.58-2.35 (m, 4H), 2.23-2.13 (m, 1H), 2.05-1.91 (m, 2H) ppm. $^{13}$C-NMR (75 MHz, CDCl$_3$): 192.7 (d), 152.4 (d), 142.7 (s), 134.9 (d), 130.4 (d), 43.0 (d), 39.8 (t), 34.6 (d), 29.3 (t), 24.3 (t) ppm. GC/MS (EI): 148 (M$^+$, 36), 133 (6), 120 (10), 105 (6), 91 (18), 77 (13), 66 (100), 55 (6), 39 (12). IR (neat, v/cm$^{-1}$): 3050 m, 2924 s, 2717 m, 1678 s, 1171 m.

EXAMPLE 36

3a,4,7,7a-Tetrahydro-1H-indene-6-carbaldehyde oxime

In analogy to Example 26, the title compound was prepared starting from 3a,4,7,7a-tetrahydro-1H-indene-6-carbaldehyde in a yield of 65%.

Odor description: spicy, floral, weak.

$^1$H-NMR (300 MHz, CDCl$_3$): 8.85 (br, OH), 7.74 (s, 1H), 6.16 (dd, J=5.1, 5.1 Hz, 1H), 5.69-5.66 (m, 1H), 5.59-5.56 (m, 1H), 2.90 (bs, 1H), 2.57-2.35 (m, 4H), 2.15-1.96 (m, 3H) ppm. $^{13}$C-NMR (75 MHz, CDCl$_3$): 152.5 (d), 136.3 (s), 135.2 (d), 134.2 (s), 130.2 (d), 42.8 (d), 39.8 (d), 34.7 (t), 28.5 (t), 26.6 (t) ppm. GC/MS (EI): 163 (M$^+$, 17), 146 (18), 129 (6), 115 (7), 91 (9), 77 (9), 66 (100), 39 (8). IR (neat, v/cm$^{-1}$): 3302br, 3047 m, 2924 s, 1631 m, 1446 m, 1311 w, 953 s.

EXAMPLE 37

(3a,4,7,7a-Tetrahydro-1H-inden-6-yl)methanol

Following the general procedure described in Example 2, the title compound (53% yield) was prepared starting from 3a,4,7,7a-tetrahydro-1H-indene-6-carbaldehyde.

Odor description: cucumber, green, nonadienol.

$^1$H-NMR (300 MHz, CDCl$_3$): 5.78-5.73 (m, 1H), 5.65-5.53 (m, 2H), 3.97 (s, 2H), 2.88-2.78 (m, 1H), 2.56-1.79 (m, 8H) ppm. GC/MS (EI): 150 (M$^+$, 1), 132 (30), 117 (25), 104 (4), 91 (16), 79 (14), 66 (100), 55 (5), 39 (9).

EXAMPLE 38

1-(3a,4,7,7a-Tetrahydro-1H-inden-6yl)ethanone

Following the general procedure described in Example 4, the title compound (30% yield) was prepared starting from 1-(3a,4,7,7a-tetrahydro-1H-inden-6-yl)ethanol.

Odor description: green, fruity, floral, melon.

$^1$H-NMR (300 MHz, CDCl$_3$): 7.05 (dd, J=5.3, 5.3 Hz, 1H), 5.67-5.63 (m, 1H), 5.56-5.51 (m, 1H), 2.97-2.88 (m, 1H), 2.70-2.34 (m, 4H), 2.28 (s, 3H), 2.11-1.92 (m, 3H) ppm. GC/MS (EI): 162 (M$^+$, 27), 147 (6), 119 (26), 97 (20), 91 (18), 77 (9), 66 (100), 53 (8), 43 (40).

EXAMPLE 39

5-Methyl-3a,4,7,7a-tetrahydro-1H-indene-6-carbaldehyde

Following the general procedure described in Example 1, the title compound (35% yield; boiling point: 90° C./0.41 mbar) was prepared starting from cyclopentadiene and prenal.

Odor description: green, fruity, melon.

$^1$H-NMR (300 MHz, CDCl$_3$): 10.04 (s, 1H), 5.61-5.58 (m, 1H), 5.46-5.43 (m, 1H), 3.04-2.94 (m, 1H), 2.59-2.46 (m, 2H), 2.40-2.28 (m, 2H), 2.16 (s, 3H), 2.13-2.00 (m, 2H), 1.93-1.81 (m, 1H) ppm. $^{13}$C-NMR (75 MHz, CDCl$_3$): 188.8 (d), 159.7 (s), 135.0 (s), 133.3 (d), 130.9 (d), 44.1 (d), 40.0 (t), 37.7 (t), 34.4 (d), 25.6 (t), 18.8 (q) ppm. GC/MS (EI): 162 (M$^+$, 46), 147 (22), 131 (10), 115 (6), 105 (9), 91 (20), 77 (14), 66 (100), 51 (6), 39 (12). IR (neat, v/cm$^{-1}$): 3048 m, 2925 s, 2848 s, 1665 s, 1632 m, 1434 m, 1377 m.

EXAMPLE 40

(5-Methyl-3a,4,7,7a-tetrahydro-1H-inden-6-yl) methanol

Following the general procedure described in Example 2, the title compound (98% yield) was prepared starting from 5-methyl-3a,4,7,7a-tetrahydro-1H-indene-6-carbaldehyde.

Odor description: spicy, hyacinth, fruity, apple, green.

$^1$H-NMR (300 MHz, CDCl$_3$): 5.67-5.63 (m, 1H), 5.53-5.47 (m, 1H), 5.17-4.08 (m, 2H), 2.96-2.85 (m, 1H), 2.61-2.44 (m, 2H), 2.27-2.15 (m, 2H), 2.04-1.82 (m, 4H), 1.75 (s, 3H) ppm. GC/MS (EI): 164 (M$^+$, 1), 146 (69), 131 (87), 117 (19), 105 (30), 91 (40), 79 (33), 66 (100), 53 (7), 41 (13). IR (neat, v/cm$^{-1}$): 3327br, 3047 m, 2925 s, 1668 w, 1444 m, 996 s.

EXAMPLE 41 rac-1-(Propan-2-ylidene)-3a,4,7,7a-tetrahydro-1H-indene-6-carbaldehyde

Following the general procedure described in Example 1, the title compound (42% yield) was prepared starting from 6,6-dimethyl fulvene and crotonic aldehyde.

Odor description: fruity, green, woody.

$^1$H-NMR (300 MHz, CDCl$_3$): 9.44 (s, 1H, CHO), 6.95 (ddd, J=5.9, 4.5, 1.5 Hz, 1H, 5-H), 6.34 (dd, J=5.7, 2.3 Hz, 1H, 2-H), 5.70 (bd, J=5.7 Hz, 1H, 3-H), 3.24-3.17 (m, 1H, 3a-H), 2.92 (ddd, J=7.5, 7.5, 7.5 Hz, 1H, 7a-H), 2.72-2.62 (m, 2H, 4-H$_a$, 7-H$_a$), 2.27-2.17 (dddd, J=16.6, 6.1, 4.5, 1.5 Hz, 1H, 4-H$_b$), 1.91 (dd, J=15.5 Hz, 8.3 Hz, 1H, 7-H$_b$), 1.79 (s, 3H, (CH$_3$)$_a$), 1.74 (s, H, CH$_3$)$_b$) ppm. $^{13}$C-NMR (75 MHz, CDCl$_3$): 192.1 (d, CHO), 151.8 (d, C-5), 143.7 (s, C-6), 142.9 (s, C-3), 136.7 (d, C-3), 131.4 (d, C-2), 122.6 (s, C(CH$_3$)$_2$), 43.4 (d, C-3a), 39.4 (d, C-7a), 29.3 (t, C-4), 23.8 (t, C-7), 21.1 (q, (CH$_3$)$_a$), 21.0 (q, (CH$_3$)$_b$) ppm. GC/MS (EI): 188 (M$^+$, 30), 173 (4), 159 (2), 145 (5), 128 (6), 115 (7), 106 (100), 91

(40), 77 (7), 65 (6), 53 (4), 39 (5). IR (neat, v/cm⁻¹): 2910 s, 2716 m, 1681 s, 1443 m, 1374 m.

EXAMPLE 42

2-Methyl-3a,4,7,7a-tetrahydro-1H-indene-6-carbaldehyde and 3-methyl-3a,4,7,7a-tetrahydro-1H-indene-6-carbaldehyde (mixture with a ratio of 2:1)

Following the general procedure described in Example 1, a mixture of 2-methyl-3a,4,7,7a-tetrahydro-1H-indene-6-carbaldehyde and 3-methyl-3a,4,7,7a-tetrahydro-1H-indene-6-carbaldehyde (35% yield) was prepared starting from methyl cyclopentadiene and crotonic aldehyde.

Odor description: green, fresh, spicy, fruity, cuminic, anisic.

$^1$H-NMR (300 MHz, CDCl$_3$): 9.45, 9.44 (2s, 1H), 6.99-6.96 (m, 1H), 5.28-5.27, 5.18-5.17 (2m, 1H), 2.98-2.93, 2.74-2.68 (2m, 1H), 2.59-2.39 (m, 4H), 2.24-2.16 (m, 1H), 2.07-2.02 (m, 1H), 1.94-1.85 (m, 1H), 1.69, 1.67 (2s, 3H) ppm. GC/MS (EI): major isomer: 162 (M⁺, 21), 147 (5), 134 (6), 115 (5), 105 (5), 91 (13), 80 (100), 65 (6), 53 (7), 39 (10). IR (neat, v/cm⁻¹): 3037 m, 2917 s, 2842 m, 1679 s, 1442 m, 1377 m, 1176 m, 831 m.

EXAMPLE 43

4-Ethyl-3a,4,7,7a-tetrahydro-1H-indene-6-carbaldehyde

Following the general procedure described in Example 1, the title compound (42% yield) was prepared starting from cyclopentadiene and 2-hexenal.

Odor description: green, fruity, weak.

$^1$H-NMR (300 MHz, CDCl$_3$): 9.42, 9.40 (2s, 1H), 6.84-6.83, 6.74-6.72 (2m, 1H), 5.74-5.53 (m, 2H), 3.26-3.13 (m, 1H), 2.87-2.75 (m, 1H), 2.66-1.46 (m, 7H), 1.06, 1.02 (2t, J=7.5 Hz, 3H) ppm. Major isomer: $^{13}$C-NMR (75 MHz, CDCl$_3$) 192.7 (d), 157.3 (d), 142.4 (s), 132.5 (d), 130.3 (d), 49.1 (d), 41.2 (d), 41.0 (t), 34.4 (d), 25.1 (t), 24.9 (t), 12.44 (q) ppm. GC/MS (EI): 176 (M⁺, 28), 147 (23), 117 (13), 105 (8), 91 (21), 77 (14), 66 (100), 41 (10). Minor isomer: $^{13}$C-NMR (75 MHz, CDCl$_3$): 192.7 (d), 156.3 (d), 142.5 (s), 133.9 (d), 130.2 (d), 49.4 (d), 41.9 (d), 39.4 (t), 35.5 (d), 27.1 (t), 24.7 (t), 11.63 (q) ppm. IR (neat, v/cm⁻¹): 3054 m, 2961 s, 2929 s, 1683 s, 1447 m.

EXAMPLE 44

1,4,4a,7,8,8a-hexahydronaphthalene-2-carbaldehyde

Following the general procedure described in Example 1, the title compound (19% yield) was prepared starting from cyclohexadiene and crotonic aldehyde.

Odor description: floral, green, spicy, woody.

$^1$H-NMR (300 MHz, CDCl$_3$): 9.39 (s, 1H), 6.70 (s, 1H), 5.59 (s, 2H), 2.60-2.49 (m, 1H), 2.39-1.98 (m, 7H), 1.54 (d, J=12.8 Hz, 1H), 1.51 (d, J=12.8 Hz, 1H) ppm. $^{13}$C-NMR (75 MHz, CDCl$_3$): 194.4 (d), 149.1 (d), 140.1 (s), 131.0 (d), 127.1 (d), 32.1 (d), 31.5 (t), 29.5 (d), 25.0 (t), 24.6 (t), 24.1 (t) ppm. GC/MS (EI): 162 (M⁺, 53), 147 (9), 133 (16), 139 (15), 115 (6), 105 (12), 91 (39), 80 (100), 65 (9), 53 (9), 39 (13). IR (neat, v/cm⁻¹):

EXAMPLE 45

4-(6-Methylhepta-1,5-dien-2-yl)cyclohex-1-enecarbaldehyde

Following the general procedure described in Example 1, the title compound (10% yield) was prepared starting from myrcene and crotonic aldehyde.

Odor description: green, fruity, fatty.

The analytical data are in accordance to the reference data of Raharivelomanana et al., Journal of Natural Products, Vol. 56(2), 1993, 272-274.

EXAMPLE 46

Fragrance Composition

A fragrance composition with a fruity, apple and spicy character

| | |
|---|---:|
| Agrumex (2-tert-butylcyclohexyl acetate) | 300 |
| 1-Vinylcyclohex-3-ene carbaldehyde | 13 |
| 4-Vinylcyclohex-1-ene carbaldehyde | 7 |
| Belembre (1,7,7-trimethy1-2'-(1-methylethyl)spiro[bicyclo[2.2.1] heptane-2,4'-[1,3]dioxane]) 50% in IPM | 10 |
| Allyl cyclohexyl propionate | 15 |
| Ethyl vanilline | 1 |
| Fraise pure (ethyl methyl phenyl glycidate) | 3 |
| Galaxolide (cyclopenta[g]-2-benzopyran, 1,3,4,6,7,8-hexahydro-4,6,6,7,8,8-hexamethyl) 66% in DEP | 200 |
| Galbanone 10 (1-(5,5-dimethylcyclohex-1-enyl)pent-4-en-1-one) | 50 |
| Jasmacyclene (4,7-Methano-1H-inden-6-ol, 3a,4,5,6,7,7a-hexahydro-, acetate) | 50 |
| Peche pure (5-heptyldihydrofuran-2(3H)-one) | 50 |
| Diethylphthalate | 50 |
| Pomarose (5,6,7-trimethylocta-2,5-dien-4-one) | 1 |
| Hercolyn DW (Methyl dihydroabietate) | 250 |
| | 1000 |

In this perfume, 1-vinylcyclohex-3-ene carbaldehyde and 4-vinylcyclohex-1-ene carbaldehyde impart a natural fresh fruitiness with a sparkling top note.

The invention claimed is:
1. A compound of formula (IVb)

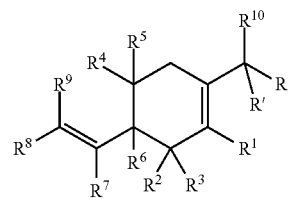

(IVb)

wherein
R$^1$ is hydrogen, methyl, or ethyl;
R$^2$ is hydrogen, C$_1$-C$_6$ alkyl, or C$_2$-C$_6$ alkenyl;
R$^3$ is hydrogen, methyl, or ethyl; or
either R$^1$ and R$^3$ or R$^2$ and R$^3$ form together with the carbon atoms to which they are attached a 5- or 6-membered carbocyclic ring;
R$^5$, R$^6$, and R$^7$ are hydrogen;
R$^4$, R$^8$ and R$^9$ are independently selected from hydrogen, C$_1$-C$_6$ alkyl, or C$_2$-C$_6$ alkenyl; or R⁴+R⁹ together is a bivalent residue selected from —(CH₂)$_n$— wherein n is 1 or 2, —C(=C(CH₃)₂)—, and —C(=C(CH₂CH₃)₂)—; and R¹⁰ is hydrogen, linear or branched C₁-C₅ alkyl, or linear or branched C₂-C₅ alkenyl;

R is hydrogen and R' is selected from hydroxyl or —OCOR¹³, wherein R¹³ is hydrogen, or C₁-C₃ alkyl;

R and R' are selected from methoxy and ethoxy; or

R and R' forming together with the carbon atom to which they are attached dioxolan, dioxane, or carbonyl;

provided that 1-(3a,4,7,7a-tetrahydro-1H-inden-6-yl)ethanone, is excluded.

2. A compound of formula (IVb) according to claim 1 selected from:
  4-vinylcyclohex-1-ene carbaldehyde,
  (4-vinylcyclohex-1-enyl)methanol,
  1-(4-vinylcyclohex-1-enyl)ethanol,
  2-methyl-4-vinylcyclohex-1-ene carbaldehyde,
  (2-methyl-4-vinylcyclohex-1-enyl)methanol,
  3a,4,7,7a-tetrahydro-1H-indene-6-carbaldehyde,
  (3a,4,7,7a-tetrahydro-1H-inden-6-yl)methanol,
  5-methyl-3a,4,7,7a-tetrahydro-1H-indene-6-carbaldehyde,
  (5-methyl-3a,4,7,7a-tetrahydro-1H-inden-6-yl)methanol,
  1-(propan-2-ylidene)-3a,4,7,7a-tetrahydro-1H-indene-6-carbaldehyde,
  2-methyl-3a,4,7,7a-tetrahydro-1H-indene-6-carbaldehyde,
  4-ethyl-3a,4,7,7a-tetrahydro-1H-indene-6-carbaldehyde, and
  1,4,4a,7,8,8a-hexahydronaphthalene-2-carbaldehyde.

3. A flavor or fragrance compound according to formula (IVb)

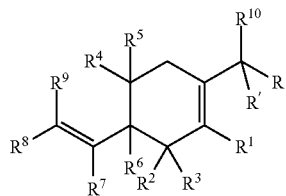

(IVb)

wherein
R¹ is hydrogen, methyl, or ethyl;
R² is hydrogen, C₁-C₆ alkyl, or C₂-C₆ alkenyl;
R³ is hydrogen, methyl, or ethyl; or
either R¹ and R³ or R² and R³ form together with the carbon atoms to which they are attached a 5- or 6-membered carbocyclic ring;
R⁵, R⁶, and R⁷ are hydrogen;
R⁴, R⁸ and R⁹ are independently selected from hydrogen, C₁-C₆ alkyl, or C₂-C₆ alkenyl; or
R⁴+R⁹ together is a bivalent residue selected from —(CH₂)$_n$— wherein n is 1 or 2, —C(=C(CH₃)₂)—, and —C(=C(CH₂CH₃)₂)—; and
R¹⁰ is hydrogen, linear or branched C₁-C₅ alkyl, or linear or branched C₂-C₅ alkenyl;
R is hydrogen and R' is selected from hydroxyl or —OCOR¹³, wherein R¹³ is hydrogen, or C₁-C₃ alkyl;
R and R' are selected from methoxy and ethoxy; or
R and R' forming together with the carbon atom to which they are attached dioxolan, dioxane, or carbonyl.

4. A compound according to formula (IVa)

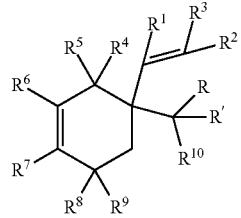

(IVa)

wherein
R¹ is hydrogen, methyl, or ethyl;
R² is hydrogen, C₁-C₆ alkyl, or C₂-C₆ alkenyl;
R³ is hydrogen, methyl, or ethyl; or
either R¹ and R³ or R² and R³ form together with the carbon atoms to which they are attached a 5- or 6-membered carbocyclic ring;
R⁴, R⁵, R⁷, R⁸ and R⁹ are independently selected from hydrogen, C₁-C₆ alkyl, and C₂-C₆ alkenyl, and R6 is independently selected from hydrogen and C₂-C₆ alkenyl; or
R⁴+R⁹ together is a bivalent residue selected from —(CH₂)$_n$— wherein n is 1 or 2, —C(=C(CH₃)₂)—, and —C(=C(CH₂CH₃)₂)—; and
R¹⁰ is hydrogen, linear or branched C₁-C₅ alkyl, or linear or branched C₂-C₅ alkenyl;
R is hydrogen and R' is selected from hydroxyl or —OCOR¹³, wherein R¹³ is hydrogen, or C₁-C₃ alkyl; or,
R and R' forming together with the carbon atom to which they are attached dioxolan, dioxane, carbonyl, or C=N—OH;
with the proviso that 4-acetoxymentha-1,8-diene and compound(s) of formula (IVa)
wherein R¹, R⁴ to R⁶, R⁸ and R⁹ are hydrogen, R⁷ is methyl and R+R' forms together with the carbon atom to which they are attached a carbonyl group or R is hydrogen and R' is hydroxyl are excluded.

5. A compound of formula (IVa) according to claim 4 selected from:
  2,4-dimethyl-1-vinylcyclohex-3-enecarbaldehyde,
  (2,4-dimethyl-1-vinylcyclohex-3-enyl)methanol,
  (2,4-dimethyl-1-vinylcyclohex-3-enyl)ethanol,
  1-(2,4-dimethyl-1-vinylcyclohex-3-enyl)ethanone,
  (2,4-dimethyl-1-vinylcyclohex-3-enyl)methyl acetate,
  (2,4-dimethyl-1-vinylcyclohex-3-enyl)but-3-en-1-ol,
  (2,4-dimethyl-1-vinylcyclohex-3-enyl)but-3-en-1-one,
  2,4-dimethyl-1-(prop-1-en-2-yl)cyclohex-3-enecarbaldehyde,
  1-(2,4-dimethyl-1-(prop-1-en-2-yl)cyclohex-3-enyl)ethanol,
  1-(2,4-dimethyl-1-(prop-1-en-2-yl)cyclohex-3-enyl)ethyl acetate,
  1-(2,4-dimethyl-1-(prop-1-en-2-yl)cyclohex-3-enyl)-2-methylpropan-1-ol,
  1-(2,4-dimethyl-1-(prop-1-en-2-yl)cyclohex-3-enyl)-2-methylpropan-1-one,
  1-(2,4-dimethyl-1-(prop-1-en-2-yl)cyclohex-3-enyl)ethanone,
  1-(2,4-dimethyl-1-(prop-1-en-2-yl)cyclohex-3-enyl)but-3-en-1-ol,
  1-(2,4-dimethyl-1-(prop-1-en-2-yl)cyclohex-3-enyl)but-3-en-1-one, 1-(2,4-dimethyl-1-(prop-1-en-2-yl)cyclohex-3-enyl)but-2-en-1-one,
1-(buta-1,3-dienyl)-2,4-dimethylcyclohex-3-enecarbaldehyde,
2-methyl-1-(2-methylprop-1-enyl)cyclohex-3-enecarbaldehyde,
2,4-dimethyl-1-(2-methylprop-1-enyl)cyclohex-3-enecarbaldehyde,
1-(2,4-dimethyl-1-(2-methylprop-1-enyl)cyclohex-3-enyl)ethanol,
1-cyclopentenyl-2,4-dimentylcyclohex-3-enecarbaldehyde,
4,5-dimethyl-2-(2-methylprop-1-enyl)-1-vinylcyclohex-3-enecarbaldeh- yde,
2-methyl-4-(4-methylpent-3-enyl)-1-vinylcyclohex-3-enecarbaldehyde,
4-methyl-1-vinyl-cyclohex-3-enecarbaldehyde oxime,
3-methyl-1-vinyl-cyclohex-3-ene-carbaldehyde oxime,
1-(prop-1-en-2-yl)cyclohex-3-enecarbaldehyde,
1-(but-1-enyl)-2,4-dimethylcyclohex-3-enecarbaldehyde,
4-methyl-1-(prop-1-en-2-yl)cyclohex-3-enecarbaldehyde,
1-vinylcyclohex-3-ene carbaldehyde, or mixtures thereof.

6. A flavor or fragrance compound of formula (IVa)

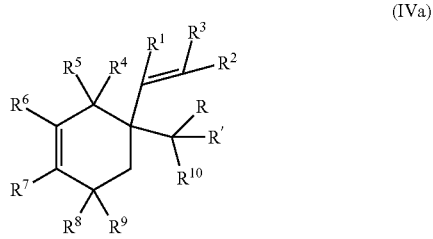

(IVa)

wherein
$R^1$ is hydrogen, methyl, or ethyl;
$R^2$ is hydrogen, $C_1$-$C_6$ alkyl, or $C_2$-$C_6$ alkenyl;
$R^3$ is hydrogen, methyl, or ethyl; or
either $R^1$ and $R^3$ or $R^2$ and $R^3$ form together with the carbon atoms to which they are attached a 5- or 6-membered carbocyclic ring;
$R^4$, $R^5$, $R^6$, $R^7$, $R^8$ and $R^9$ are independently selected from hydrogen, $C_1$-$C_6$ alkyl, or $C_2$-$C_6$ alkenyl; or
$R^4+R^9$ together is a bivalent residue selected from —(CH$_2$)$_n$— wherein n is 1 or 2, —C(=C(CH$_3$)$_2$)—, and —C(=C(CH$_2$CH$_3$)$_2$)—; and
$R^{10}$ is hydrogen, linear or branched $C_1$-$C_5$ alkyl, or linear or branched $C_2$-$C_5$ alkenyl;
R is hydrogen and R' is selected from hydroxyl or —OCOR$^{13}$, wherein $R^{13}$ is hydrogen, or $C_1$-$C_3$ alkyl;
R and R' are selected from methoxy and ethoxy; or
R and R' forming together with the carbon atom to which they are attached dioxolan, carbonyl, dioxane, or C=N—OH;
with the proviso that 4-acetoxymentha-1,8-diene and compound(s) of formula (IVa) wherein $R^1$, $R^4$ to $R^6$, $R^8$ and $R^9$ are hydrogen, $R^7$ is methyl and R+R' forms together with the carbon atom to which they are attached a carbonyl group or R is hydrogen and R' is hydroxyl are excluded.

7. A method for improving, enhancing or modifying a consumer product base comprising the step of: adding to the consumer product base a flavour or fragrance compound of formulae (IVa):

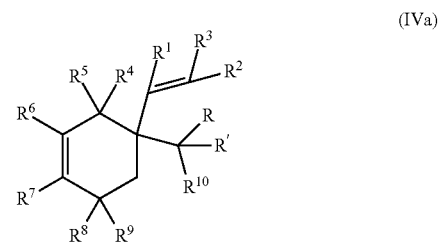

(IVa)

wherein
$R^1$ is hydrogen, methyl, or ethyl;
$R^2$ is hydrogen, $C_1$-$C_6$ alkyl, or $C_2$-$C_6$ alkenyl;
$R^3$ is hydrogen, methyl, or ethyl; or
either $R^1$ and $R^3$ or $R^2$ and $R^3$ form together with the carbon atoms to which they are attached a 5- or 6-membered carbocyclic ring;
$R^4$, $R^5$, $R^6$, $R^7$, $R^8$ and $R^9$ are independently selected from hydrogen, $C_1$-$C_6$ alkyl, or $C_2$-$C_6$ alkenyl; or
$R^4+R^9$ together is a bivalent residue selected from —(CH$_2$)$_n$— wherein n is 1 or 2, —C(=C(CH$_3$)$_2$)—, and —C(=C(CH$_2$CH$_3$)$_2$)—; and
$R^{10}$ is hydrogen, linear or branched $C_1$-$C_5$ alkyl, or linear or branched $C_2$-$C_5$ alkenyl;
R is hydrogen and R' is selected from hydroxyl or —OCOR$^{13}$, wherein $R^{13}$ is hydrogen, or $C_1$-$C_3$ alkyl;
R and R' are selected from methoxy and ethoxy; or
R and R' forming together with the carbon atom to which they are attached dioxolan, carbonyl, dioxane, or C=N—OH;
with the proviso that 4-acetoxymentha-1,8-diene and compound(s) of formula (IVa) wherein $R^1$, $R^4$ to $R^6$, $R^8$ and $R^9$ are hydrogen, $R^7$ is methyl and R+R' forms together with the carbon atom to which they are attached a carbonyl group or R is hydrogen and R' is hydroxyl are excluded.

8. A method for improving, enhancing or modifying a consumer product base comprising the step of: adding to the consumer base a compound of formula (IVb)

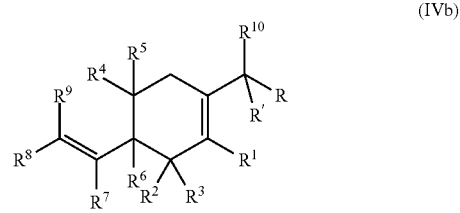

(IVb)

wherein
$R^1$ is hydrogen, methyl, or ethyl;
$R^2$ is hydrogen, $C_1$-$C_6$ alkyl, or $C_2$-$C_6$ alkenyl;
$R^3$ is hydrogen, methyl, or ethyl; or
either $R^1$ and $R^3$ or $R^2$ and $R^3$ form together with the carbon atoms to which they are attached a 5- or 6-membered carbocyclic ring;
$R^5$, $R^6$, and $R^7$ are hydrogen;
$R^4$, $R^8$ and $R^9$ are independently selected from hydrogen, $C_1$-$C_6$ alkyl, or $C_2$-$C_6$ alkenyl; or
$R^4+R^9$ together is a bivalent residue selected from —(CH$_2$)$_n$— wherein n is 1 or 2, —C(=C(CH$_3$)$_2$)—, and —C(=C(CH$_2$CH$_3$)$_2$)—; and
$R^{10}$ is hydrogen, linear or branched $C_1$-$C_5$ alkyl, or linear or branched $C_2$-$C_5$ alkenyl;

R is hydrogen and R' is selected from hydroxyl or —OCOR$^{13}$, wherein R$^{13}$ is hydrogen, or C$_1$-C$_3$ alkyl;
R and R' are selected from methoxy and ethoxy; or
R and R' forming together with the carbon atom to which they are attached dioxolan, dioxane, or carbonyl.

9. A fragrance application comprising:
a) as odorant, at least one compound of formula (IVa);

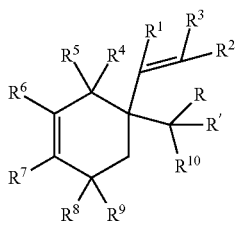
(IVa)

wherein
R$^1$ is hydrogen, methyl, or ethyl;
R$^2$ is hydrogen, C$_1$-C$_6$ alkyl, or C$_2$-C$_6$ alkenyl;
R$^3$ is hydrogen, methyl, or ethyl; or
either R$^1$ and R$^3$ or R$^2$ and R$^3$ form together with the carbon atoms to which they are attached a 5- or 6-membered carbocyclic ring;
R$^4$, R$^5$, R$^6$, R$^7$, R$^8$ and R$^9$ are independently selected from hydrogen, C$_1$-C$_6$ alkyl, or C$_2$-C$_6$ alkenyl; or
R$^4$+R$^9$ together is a bivalent residue selected from —(CH$_2$)$_n$— wherein n is 1 or 2, —C(=C(CH$_3$)$_2$)—, and —C(=C(CH$_2$CH$_3$)$_2$)—; and
R$^{10}$ is hydrogen, linear or branched C$_1$-C$_5$ alkyl, or linear or branched C$_2$-C$_5$ alkenyl;
R is hydrogen and R' is selected from hydroxyl or —OCOR$^{13}$, wherein R$^{13}$ is hydrogen, or C$_1$-C$_3$ alkyl;
R and R' are selected from methoxy and ethoxy; or
R and R' forming together with the carbon atom to which they are attached dioxolan, carbonyl, dioxane, or C=N—OH;
with the proviso that 4-acetoxymentha-1,8-diene and compound(s) of formula (IVa) wherein R$^1$, R$^4$ to R$^6$, R$^8$ and R$^9$ are hydrogen, R$^7$ is methyl and R+R' forms together with the carbon atom to which they are attached a carbonyl group or R is hydrogen and R' is hydroxyl are excluded
and
b) a consumer product base.

10. A process comprising the step of:
reacting formylbutadiene of formula B

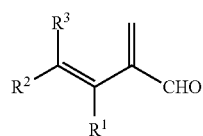
B wherein
R$^1$ is hydrogen, methyl, or ethyl;
R$^2$ is hydrogen, C$_1$-C$_6$ alkyl, or C$_2$-C$_6$ alkenyl;
R$^3$ is hydrogen, methyl, or ethyl; or
either R$^1$ and R$^3$ or R$^2$ and R$^3$ form together with the carbon atoms to which they are attached a 5- or 6-membered carbocyclic ring;

with a diene of formula C

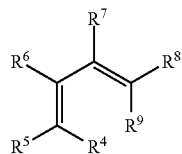
C wherein
R$^4$, R$^5$, R$^6$, R$^7$, R$^8$ and R$^9$ are independently selected from hydrogen, C$_1$-C$_6$ alkyl, or C$_2$-C$_6$ alkenyl; or
R$^4$+R$^9$ together is a bivalent residue selected from —(CH$_2$)$_n$— wherein n is 1 or 2, —C(=C(CH$_3$)$_2$)—, and —C(=C(CH$_2$CH$_3$)$_2$)—;
resulting in the production of a compound formulae (Ia) or (Ib)

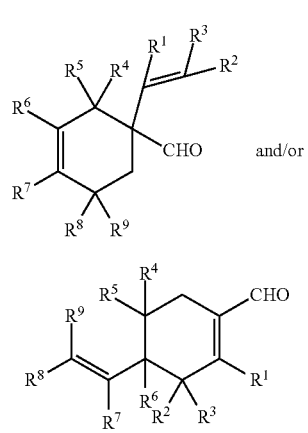
(Ia)
and/or
(Ib)

characterized in that the formylbutadiene of formula B is prepared in situ from an α,β-unsaturated aldehyde of formula A

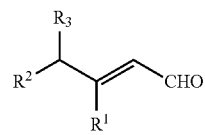
A in the presence of a methylenation catalyst and formalin.

11. A process according to claim 10 comprising the further process step of: the subsequent reduction of a compound of formula (Ia) resulting in the production of a compound of formula (IIa)

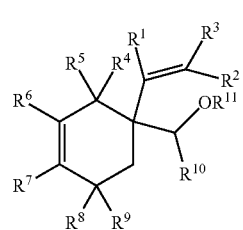
(IIa)

wherein
R$^1$ is hydrogen, methyl, or ethyl;
R$^2$ is hydrogen, C$_1$-C$_6$ alkyl, or C$_2$-C$_6$ alkenyl;
R$^3$ is hydrogen, methyl or ethyl; or
either R$^1$ and R$^3$ or R$^2$ and R$^3$ form together with the carbon atoms to which they are attached a 5- or 6-membered carbocyclic ring;
R$^4$, R$^5$, R$^6$, R$^7$, R$^8$ and R$^9$ are independently selected from hydrogen, C$_1$-C$_6$ alkyl, or C$_2$-C$_6$ alkenyl; or
R$^4$+R$^9$ together is a bivalent residue selected from —(CH$_2$)$_n$— wherein n is 1 or 2, —C(=C(CH$_3$)$_2$)—, and —C(=C(CH$_2$CH$_3$)$_2$)—;
R$^{10}$ is hydrogen, linear or branched C$_1$-C$_5$ alkyl, or linear or branched C$_2$-C$_5$ alkenyl; and
R$^{11}$ is hydrogen.

12. A process according to claim 11 comprising the further process step of: the subsequent esterification of a compound of formula (Ia) in the presence of a carboxylic acid halide and a base resulting in the production of a compound of formula (IIa) wherein R$^{11}$ is COR$^{12}$, wherein R$^{12}$ is hydrogen, or a linear or branched C$_1$-C$_3$ alkyl.

13. A process according to claim 11 comprising the further process step of: the subsequent oxidation of a compound of formula (IIa) in the presence of an oxidizing agent resulting in the production of a compound of formula (IIIa)

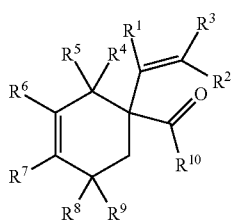

(IIIa)

wherein
R$^1$ is hydrogen, methyl, or ethyl;
R$^2$ is hydrogen, C$_1$-C$_6$ alkyl, or C$_2$-C$_6$ alkenyl;
R$^3$ is hydrogen, methyl, or ethyl; or
either R$^1$ and R$^3$ or R$^2$ and R$^3$ form together with the carbon atoms to which they are attached a 5- or 6-membered carbocyclic ring;
R$^4$, R$^5$, R$^6$, R$^7$, R$^8$ and R$^9$ are independently selected from hydrogen, C$_1$-C$_6$ alkyl, or C$_2$-C$_6$ alkenyl; or
R$^4$+R$^9$ together is a bivalent residue selected from —(CH$_2$)$_n$— wherein n is 1 or 2, —C(=C(CH$_3$)$_2$)—, and —C(=C(CH$_2$CH$_3$)$_2$)—; and
R$^{10}$ is linear or branched C$_1$-C$_5$ alkyl, or linear or branched C$_2$-C$_5$ alkenyl.

14. A process according to claim 10 comprising the further process step of: the subsequent transformation of the carbonyl group of a compound selected from compounds of formulae (Ia) and (IIIa) in the presence of
a) hydroxylamine;
b) methanol or ethanol; or
c) a diol;

resulting in a compound according to formula (IVa)

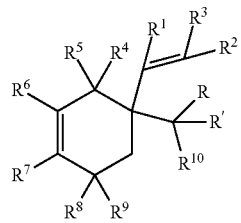

(IVa)

wherein
R$^1$ is hydrogen, methyl, or ethyl;
R$^2$ is hydrogen, C$_1$-C$_6$ alkyl, or C$_2$-C$_6$ alkenyl;
R$^3$ is hydrogen, methyl, or ethyl; or
either R$^1$ and R$^3$ or R$^2$ and R$^3$ form together with the carbon atoms to which they are attached a 5- or 6-membered carbocyclic ring;
R$^4$, R$^5$, R$^6$, R$^7$, R$^8$ and R$^9$ are independently selected from hydrogen, C$_1$-C$_6$ alkyl, or C$_2$-C$_6$ alkenyl; or
R$^4$+R$^9$ together is a bivalent residue selected from —(CH$_2$)$_n$— wherein n is 1 or 2, —C(=C(CH$_3$)$_2$)—, and —C(=C(CH$_2$CH$_3$)$_2$)—; and
R$^{10}$ is hydrogen, linear or branched C$_1$-C$_5$ alkyl, or linear or branched C$_2$-C$_5$ alkenyl;
R is hydrogen and R' is selected from hydroxyl or —OCOR$^{13}$, wherein R$^{13}$ is hydrogen, or C$_1$-C$_3$ alkyl;
R and R' are selected from methoxy and ethoxy; or
R and R' forming together with the carbon atom to which they are attached dioxolan, carbonyl, dioxane, or C=N—OH.

15. A process according to claim 10 comprising the further process step of: the subsequent reduction of a compound of formula (Ib) resulting in a compound of formula (IIb)

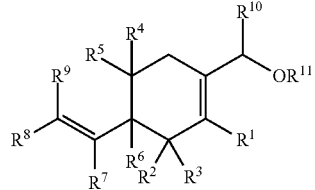

(IIb)

wherein
R$^1$ is hydrogen, methyl, or ethyl;
R$^2$ is hydrogen, C$_1$-C$_6$ alkyl, or C$_2$-C$_6$ alkenyl;
R$^3$ is hydrogen, methyl, or ethyl; or
either R$^1$ and R$^3$ or R$^2$ and R$^3$ form together with the carbon atoms to which they are attached a 5- or 6-membered carbocyclic ring;
R$^4$, R$^5$, R$^6$, R$^7$, R$^8$ and R$^9$ are independently selected from hydrogen, C$_1$-C$_6$ alkyl, or C$_2$-C$_6$ alkenyl; or
R$^4$+R$^9$ together is a bivalent residue selected from —(CH$_2$)$_n$— wherein n is 1 or 2, —C(=C(CH$_3$)$_2$)—, and —C(=C(CH$_2$CH$_3$)$_2$)—;
R$^{10}$ is hydrogen, linear or branched C$_1$-C$_5$ alkyl, or linear or branched C$_2$-C$_5$ alkenyl; and
R$^{11}$ is hydrogen.

16. A process according to claim 15 comprising the further process step of: the subsequent esterification of a compound of formula (IIb) wherein R$^{11}$ is hydrogen in the presence of carboxylic acid halides and a base resulting in a compound of formula (IIb) wherein R$^{11}$ is COR$^{12}$, wherein R$^{12}$ is hydrogen, or linear or branched C$_1$-C$_3$ alkyl.

17. A process according to claim 15 comprising the further process step of: the subsequent oxidation of a compound of formula (IIb) in the presence of an oxidizing agent resulting in a compound of formula (IIIb)

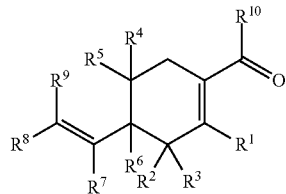

(IIIb)

wherein
$R^1$ is hydrogen, methyl, or ethyl;
$R^2$ is hydrogen, $C_1$-$C_6$ alkyl, or $C_2$-$C_6$ alkenyl;
$R^3$ is hydrogen, methyl, or ethyl; or
either $R^1$ and $R^3$ or $R^2$ and $R^3$ form together with the carbon atoms to which they are attached a 5- or 6-membered carbocyclic ring;
$R^4$, $R^5$, $R^6$, $R^7$, $R^8$ and $R^9$ are independently selected from hydrogen, $C_1$-$C_6$ alkyl, or $C_2$-$C_6$ alkenyl; or
$R^4$+$R^9$ together is a bivalent residue selected from —$(CH_2)_n$— wherein n is 1 or 2, —$C(=C(CH_3)_2)$—, and —$C(=C(CH_2CH_3)_2)$—; and
$R^{10}$ is linear or branched $C_1$-$C_5$ alkyl, or linear or branched $C_2$-$C_5$ alkenyl.

18. A process according to claim 10 comprising the further process step of: the subsequent transformation of the carbonyl group of a compound selected from compounds of formulae (Ia) and (IIIa) in the presence of
a) hydroxylamine;
b) methanol or ethanol; or
c) a diol;
resulting in a compound of formula (IVb)

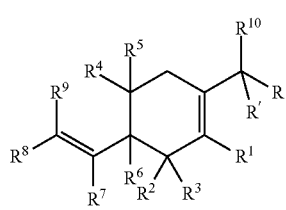

(IVb)

wherein
$R^1$ is hydrogen, methyl, or ethyl;
$R^2$ is hydrogen, $C_1$-$C_6$ alkyl, or $C_2$-$C_6$ alkenyl;
$R^3$ is hydrogen, methyl, or ethyl; or
either $R^1$ and $R^3$ or $R^2$ and $R^3$ form together with the carbon atoms to which they are attached a 5- or 6-membered carbocyclic ring;
$R^4$, $R^5$, $R^6$, $R^7$, $R^8$ and $R^9$ are independently selected from hydrogen, $C_1$-$C_6$ alkyl, or $C_2$-$C_6$ alkenyl; or
$R^4$+$R^9$ together is a bivalent residue selected from —$(CH_2)_n$— wherein n is 1 or 2, —$C(=C(CH_3)_2)$—, and —$C(=C(CH_2CH_3)_2)$—; and
$R^{10}$ is hydrogen, linear or branched $C_1$-$C_5$ alkyl, or linear or branched $C_2$-$C_5$ alkenyl;
R is hydrogen and R' is selected from hydroxyl or —$OCOR^{13}$, wherein $R^{13}$ is hydrogen, or $C_1$-$C_3$ alkyl;
R and R' are selected from methoxy and ethoxy; or
R and R' forming together with the carbon atom to which they are attached dioxolan, carbonyl, dioxane, or C=N—OH.

19. A fragrance application comprising:
a) as odorant, at least one compound selected from compounds of formula (IVb)

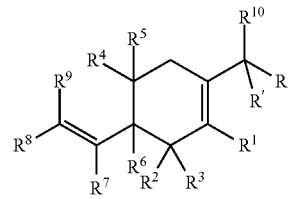

(IVb)

wherein
$R^1$ is hydrogen, methyl, or ethyl;
$R^2$ is hydrogen, $C_1$-$C_6$ alkyl, or $C_2$-$C_6$ alkenyl;
$R^3$ is hydrogen, methyl, or ethyl; or
either $R^1$ and $R^3$ or $R^2$ and $R^3$ form together with the carbon atoms to which they are attached a 5- or 6-membered carbocyclic ring;
$R^5$, $R^6$, and $R^7$ are hydrogen;
$R^4$, $R^8$ and $R^9$ are independently selected from hydrogen, $C_1$-$C_6$ alkyl, or $C_2$-$C_6$ alkenyl; or
$R^4$+$R^9$ together is a bivalent residue selected from —$(CH_2)_n$— wherein n is 1 or 2, —$C(=C(CH_3)_2)$—, and —$C(=C(CH_2CH_3)_2)$—; and
$R^{10}$ is hydrogen, linear or branched $C_1$-$C_5$ alkyl, or linear or branched $C_2$-$C_5$ alkenyl;
R is hydrogen and R' is selected from hydroxyl or —$OCOR^{13}$, wherein $R^{13}$ is hydrogen, or $C_1$-$C_3$ alkyl;
R and R' are selected from methoxy and ethoxy; or
R and R' forming together with the carbon atom to which they are attached dioxolan, dioxane, or carbonyl;
and
b) a consumer product base.

20. A process according to claim 13 comprising the further process step of the subsequent transformation of the carbonyl group of a compound selected from compounds of formulae (Ia) and (IIIa) in the presence of
a) hydroxylamine;
b) methanol or ethanol; or
c) a diol;
resulting in a compound of formula (IVa)

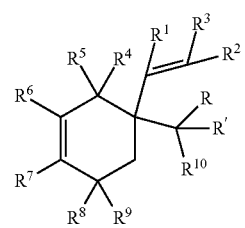

(IVa)

wherein
$R^1$ is hydrogen, methyl, or ethyl;
$R^2$ is hydrogen, $C_1$-$C_6$ alkyl, or $C_2$-$C_6$ alkenyl;
$R^3$ is hydrogen, methyl, or ethyl; or
either $R^1$ and $R^3$ or $R^2$ and $R^3$ form together with the carbon atoms to which they are attached a 5- or 6-membered carbocyclic ring;

$R^4$, $R^5$, $R^6$, $R^7$, $R^8$ and $R^9$ are independently selected from hydrogen, $C_1$-$C_6$ alkyl, or $C_2$-$C_6$ alkenyl; or $R^4$+$R^9$ together is a bivalent residue selected from —$(CH_2)_n$— wherein n is 1 or 2, —$C(=C(CH_3)_2)$—, and —$C(=C(CH_2CH_3)_2)$—; and $R^{10}$ is hydrogen, linear or branched $C_1$-$C_5$ alkyl, or linear or branched $C_2$-$C_5$ alkenyl;

R is hydrogen and R' is selected from hydroxyl or —$OCOR^{13}$, wherein $R^{13}$ is hydrogen, or $C_1$-$C_3$ alkyl;

R and R' are selected from methoxy and ethoxy; or

R and R' forming together with the carbon atom to which they are attached dioxolan.

21. A process according to claim 18 comprising the further process step of the subsequent transformation of the carbonyl group of a compound selected from compounds of formulae (Ia) and (IIIa) in the presence of
a) hydroxylamine;
b) methanol or ethanol; or
c) a diol;
resulting in a compound of formula (IVa)

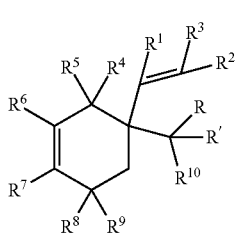

(IVa)

wherein
$R^1$ is hydrogen, methyl, or ethyl;
$R^2$ is hydrogen, $C_1$-$C_6$ alkyl, or $C_2$-$C_6$ alkenyl;
$R^3$ is hydrogen, methyl, or ethyl; or
either $R^1$ and $R^3$ or $R^2$ and $R^3$ form together with the carbon atoms to which they are attached a 5- or 6-membered carbocyclic ring;
$R^4$, $R^5$, $R^6$, $R^7$, $R^8$ and $R^9$ are independently selected from hydrogen, $C_1$-$C_6$ alkyl, or $C_2$-$C_6$ alkenyl; or
$R^4$+$R^9$ together is a bivalent residue selected from —$(CH_2)_n$— wherein n is 1 or 2, —$C(=C(CH_3)_2)$—, and —$C(=C(CH_2CH_3)_2)$—; and
$R^{10}$ is hydrogen, linear or branched $C_1$-$C_5$ alkyl, or linear or branched $C_2$-$C_5$ alkenyl;
R is hydrogen and R' is selected from hydroxyl or —$OCOR^{13}$, wherein $R^{13}$ is hydrogen, or $C_1$-$C_3$ alkyl;
R and R' are selected from methoxy and ethoxy; or
R and R' forming together with the carbon atom to which they are attached dioxolan, carbonyl, dioxane, or C=N—OH.

22. An entrapped compound of formula (IVb)

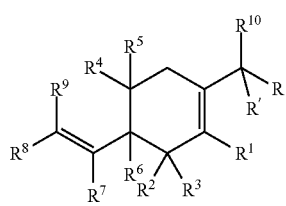

(IVb)

wherein
$R^1$ is hydrogen, methyl, or ethyl;
$R^2$ is hydrogen, $C_1$-$C_6$ alkyl, or $C_2$-$C_6$ alkenyl;
$R^3$ is hydrogen, methyl, or ethyl; or
either $R^1$ and $R^3$ or $R^2$ and $R^3$ form together with the carbon atoms to which they are attached a 5- or 6-membered carbocyclic ring;
$R^5$, $R^6$, and $R^7$ are hydrogen;
$R^4$, $R^8$ and $R^9$ are independently selected from hydrogen, $C_1$-$C_6$ alkyl, or $C_2$-$C_6$ alkenyl; or
$R^4$+$R^9$ together is a bivalent residue selected from —$(CH_2)_n$— wherein n is 1 or 2, —$C(=C(CH_3)_2)$—, and —$C(=C(CH_2CH_3)_2)$—; and
$R^{10}$ is hydrogen, linear or branched $C_1$-$C_5$ alkyl, or linear or branched $C_2$-$C_5$ alkenyl;
R is hydrogen and R' is selected from hydroxyl or —$OCOR^{13}$, wherein $R^{13}$ is hydrogen, or $C_1$-$C_3$ alkyl;
R and R' are selected from methoxy and ethoxy; or
R and R' forming together with the carbon atom to which they are attached dioxolan, dioxane, or carbonyl;
provided that 1-(3a,4,7,7a-tetrahydro-1H-inden-6-yl)ethanone, is excluded.

23. An entrapped compound of formula (IVa)

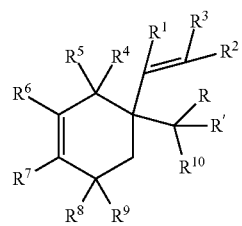

(IVa)

wherein
$R^1$ is hydrogen, methyl, or ethyl;
$R^2$ is hydrogen, $C_1$-$C_6$ alkyl, or $C_2$-$C_6$ alkenyl;
$R^3$ is hydrogen, methyl, or ethyl; or
either $R^1$ and $R^3$ or $R^2$ and $R^3$ form together with the carbon atoms to which they are attached a 5- or 6-membered carbocyclic ring;
$R^4$, $R^5$, $R^6$, $R^7$, $R^8$ and $R^9$ are independently selected from hydrogen, $C_1$-$C_6$ alkyl, or $C_2$-$C_6$ alkenyl; or
$R^4$+$R^9$ together is a bivalent residue selected from —$(CH_2)_n$— wherein n is 1 or 2, —$C(=C(CH_3)_2)$—, and —$C(=C(CH_2CH_3)_2)$—; and
$R^{10}$ is hydrogen, linear or branched $C_1$-$C_5$ alkyl, or linear or branched $C_2$-$C_5$ alkenyl;
R is hydrogen and R' is selected from hydroxyl or —$OCOR^{13}$, wherein $R^{13}$ is hydrogen, or $C_1$-$C_3$ alkyl;
R and R' are selected from methoxy and ethoxy; or
R and R' forming together with the carbon atom to which they are attached dioxolan, dioxane, carbonyl, or C=N—OH;
with the proviso that 4-acetoxymentha-1,8-diene and compound(s) of formula (IVa) wherein $R^1$, $R^4$ to $R^6$, $R^8$ and $R^9$ are hydrogen, $R^7$ is methyl and R+R' forms together with the carbon atom to which they are attached a carbonyl group or R is hydrogen and R' is hydroxyl are excluded.

24. A method according to claim 7 comprising the step of: adding thereto a compound of formula (IVb)

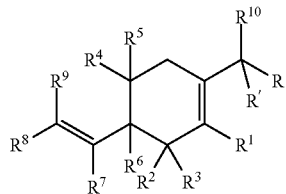

wherein
$R^1$ is hydrogen, methyl, or ethyl;
$R^2$ is hydrogen, $C_1$-$C_6$ alkyl, or $C_2$-$C_6$ alkenyl;
$R^3$ is hydrogen, methyl, or ethyl; or
either $R^1$ and $R^3$ or $R^2$ and $R^3$ form together with the carbon atoms to which they are attached a 5- or 6-membered carbocyclic ring;
$R^5$, $R^6$, and $R^7$ are hydrogen;
$R^4$, $R^8$ and $R^9$ are independently selected from hydrogen, $C_1$-$C_6$ alkyl, or $C_2$-$C_6$ alkenyl; or
$R^4$+$R^9$ together is a bivalent residue selected from —$(CH_2)_n$— wherein n is 1 or 2, —$C(=C(CH_3)_2)$—, and —$C(=C(CH_2CH_3)_2)$—; and
$R^{10}$ is hydrogen, linear or branched $C_1$-$C_5$ alkyl, or linear or branched $C_2$-$C_5$ alkenyl;
R is hydrogen and R' is selected from hydroxyl or —$OCOR^{13}$, wherein $R^{13}$ is hydrogen, or $C_1$-$C_3$ alkyl;
R and R' are selected from methoxy and ethoxy; or
R and R' forming together with the carbon atom to which they are attached dioxolan, dioxane, or carbonyl.

25. A fragrance application according to claim 9 further comprising a compound of formula (IVb)

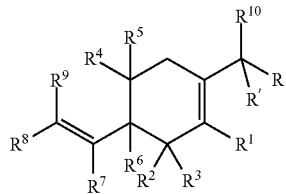

wherein
$R^1$ is hydrogen, methyl, or ethyl;
$R^2$ is hydrogen, $C_1$-$C_6$ alkyl, or $C_2$-$C_6$ alkenyl;
$R^3$ is hydrogen, methyl, or ethyl; or
either $R^1$ and $R^3$ or $R^2$ and $R^3$ form together with the carbon atoms to which they are attached a 5- or 6-membered carbocyclic ring;
$R^5$, $R^6$, and $R^7$ are hydrogen;
$R^4$, $R^8$ and $R^9$ are independently selected from hydrogen, $C_1$-$C_6$ alkyl, or $C_2$-$C_6$ alkenyl; or
$R^4$+$R^9$ together is a bivalent residue selected from —$(CH_2)_n$— wherein n is 1 or 2, —$C(=C(CH_3)_2)$—, and —$C(=C(CH_2CH_3)_2)$—; and
$R^{10}$ is hydrogen, linear or branched $C_1$-$C_5$ alkyl, or linear or branched $C_2$-$C_5$ alkenyl;
R is hydrogen and R' is selected from hydroxyl or —$OCOR^{13}$, wherein $R^{13}$ is hydrogen, or $C_1$-$C_3$ alkyl;
R and R' are selected from methoxy and ethoxy; or
R and R' forming together with the carbon atom to which they are attached dioxolan, dioxane, or carbonyl.

26. A compound according to claim 4 wherein in the compound of formula (IVa)

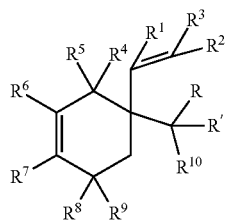

$R^1$ is hydrogen, methyl, or ethyl;
$R^2$ is hydrogen, $C_1$-$C_6$ alkyl, or $C_2$-$C_6$ alkenyl;
$R^3$ is hydrogen, methyl, or ethyl; or
either $R^1$ and $R^3$ or $R^2$ and $R^3$ form together with the carbon atoms to which they are attached a 5- or 6-membered carbocyclic ring;
$R^4$, $R^5$, $R^6$; $R^7$, $R^8$ and $R^9$ are independently selected from hydrogen, and $C_2$-$C_6$ alkenyl ; or
$R^4$+$R^9$ together is a bivalent residue selected from —$(CH_2)_n$—wherein n is 1 or 2, —$C(=C(CH_3)_2)$— and —$C(=C(CH_2CH_3)_2)$—; and
$R^{10}$ is hydrogen, linear or branched $C_1$-$O_5$ alkyl, or linear or branched $C_2$-$O_5$ alkenyl;
R is hydrogen and R' is selected from hydroxyl or —$OCOR^{13}$, wherein $R^{13}$ is hydrogen, or $C_1$-$C_3$ alkyl;
R and R' are selected from methoxy and ethoxy; or
R and R' forming together with the carbon atom to which they are attached dioxolan, dioxane, carbonyl, or C=N-OH;
with the proviso that 4-acetoxymentha-1,8-diene and compound(s) of formula (IVa) wherein $R^1$, $R^4$ to $R^6$, $R^8$ and $R^9$ are hydrogen, $R^7$ is methyl and R+R' forms together with the carbon atom to which they are attached a carbonyl group or R is hydrogen and R' is hydroxyl are excluded.

* * * * *